(12) United States Patent
Yamamoto

(10) Patent No.: US 11,781,165 B2
(45) Date of Patent: Oct. 10, 2023

(54) METHOD FOR PRODUCING SEDOHEPTULOSE

(71) Applicant: NAGASE & CO., LTD., Osaka (JP)

(72) Inventor: Shogo Yamamoto, Kobe (JP)

(73) Assignee: NAGASE & CO., LTD., Osaka (JP)

( * ) Notice: Subject to any disclaimer, the term of this patent is extended or adjusted under 35 U.S.C. 154(b) by 83 days.

(21) Appl. No.: 17/049,789

(22) PCT Filed: Apr. 26, 2019

(86) PCT No.: PCT/JP2019/017832
§ 371 (c)(1),
(2) Date: Oct. 22, 2020

(87) PCT Pub. No.: WO2019/208747
PCT Pub. Date: Oct. 31, 2019

(65) Prior Publication Data
US 2021/0246475 A1    Aug. 12, 2021

(30) Foreign Application Priority Data
Apr. 27, 2018 (JP) .................. 2018-087503

(51) Int. Cl.
*C12P 19/02* (2006.01)
*C12N 9/10* (2006.01)
*C12N 9/90* (2006.01)
*C12N 9/00* (2006.01)

(52) U.S. Cl.
CPC ............ *C12P 19/02* (2013.01); *C12N 9/1022* (2013.01); *C12N 9/90* (2013.01); *C12N 9/93* (2013.01); *C12Y 202/01002* (2013.01); *C12Y 504/99016* (2013.01); *C12Y 604/01003* (2013.01)

(58) Field of Classification Search
CPC ......... C12P 19/02; C12N 9/1022; C12N 9/90; C12N 9/93; C12Y 202/01002; C12Y 504/99016; C12Y 604/01003
See application file for complete search history.

(56) References Cited

FOREIGN PATENT DOCUMENTS

| | | |
|---|---|---|
| EP | 1 174 508 A2 | 1/2002 |
| JP | 39-14500 B | 7/1964 |
| JP | 41-4400 B | 3/1966 |
| JP | 41-5915 B | 3/1966 |
| JP | 41-21760 B | 12/1966 |
| JP | 62-126990 A | 6/1987 |
| SK | 284 318 B6 | 1/2005 |

OTHER PUBLICATIONS

Schaaff et al. Molecular analysis of the structural gene for yeast transaldolase. Eur. J. Biochem. (1990), 188: 597-603.*
International Search Report dated Jul. 16, 2019 in PCT/JP2019/017832 filed Apr. 26, 2019, 1 page.
Okuda et al., "Accumulation of Sedoheptulose by Streptomycetes", The Journal of Biochemistry, 1963, vol. 54, No. 1, pp. 107-108.
Dalmas et al., "An Efficient Synthesis of Sedoheptulose Catalyzed by Spinach Transketolase", 1993, Tetrahedron: Asymmetry, vol. 4, No. 6, pp. 1169-1172.
Villafranca et al., "Heptulose Synthesis from Nonphosphorylated Aldoses and Ketoses by Spinach Transketolase", The Journal of Biological Chemistry, 1971, vol. 246, No. 10, pp. 3126-3131 (7 total pages).
Arabolaza et al., "Crystal Structures and Mutational Analyses of Acyl-CoA Carboxylase β Subunit of *Streptomyces coelicolor*", Biochemistry, 2010, vol. 49, No. 34, pp. 1-21.
Mitova et al., "Subinhibitory Concentrations of Antibiotics Induce Phenazine Production in a Marine *Streptomyces* sp.", Journal of Natural Products, 2008, vol. 71, No. 5, pp. 824-827.
Schaaff et al., "Molecular analysis of the structural gene for yeast transaldolase", European Journal of Biochemistry, 1990, vol. 188, pp. 597-603, ISSN: 0014-2956.
Extended European Search Report dated Jan. 4, 2022 in European Patent Application No. 19791770.1, 8 pages.
Yota Tsuge, et al., "Metabolic engineering of *Corynebacterium glutamicum* for production of sunscreen shinorine," Bioscience, Biotechnology, and Biochemistry, vol. 82, No. 7, XP055751051, 2018, 9 pages.
International Preliminary Report on Patentability and Written Opinion dated Nov. 5, 2020 in PCT/JP2019/017832 (with English Translation), 11 pages.

* cited by examiner

*Primary Examiner* — Iqbal H Chowdhury
(74) *Attorney, Agent, or Firm* — Oblon, McClelland, Maier & Neustadt, L.L.P.

(57) ABSTRACT

Sedoheptulose, which is a saccharide falling within the categories of ketoses and heptuloses, is one of a small number of heptuloses occurring in nature. A method for producing sedoheptulose may use a bacterium, and/or may improve the productivity of sedoheptulose by the bacterium, and the bacterium. To solve this problem, provided are a method for producing sedoheptulose using a bacterium owing to the deletion or attenuation of a specific enzymatic function, a method for improving the productivity of sedoheptulose by the bacterium, and the bacterium.

10 Claims, 2 Drawing Sheets
Specification includes a Sequence Listing.

```
SEQUENCE LISTING

<160> NUMBER OF SEQ ID NOS: 32

<210> SEQ ID NO 1
<211> LENGTH: 372
<212> TYPE: PRT
<213> ORGANISM: Streptomyces lividans

<400> SEQUENCE: 1

Met Thr Asp Ala Leu Lys Arg Leu Ser Asp Glu Gly Val Ala Ile Trp
1               5                   10                  15

Leu Asp Asp Leu Ser Arg Lys Arg Ile Thr Ser Gly Asn Leu Ala Glu
            20                  25                  30

Leu Ile Asp Gln Gln His Val Val Gly Val Thr Thr Asn Pro Ser Ile
        35                  40                  45

Phe Gln Lys Ala Ile Ser Gln Gly Asp Gly Tyr Asp Gln Gln Leu Ala
    50                  55                  60

Asp Leu Ala Val Arg Gly Val Thr Val Glu Glu Ala Ile Arg Met Ile
65                  70                  75                  80

Thr Thr Ala Asp Val Arg Asp Ala Ala Asp Ile Leu Arg Pro Val Tyr
                85                  90                  95

Asp Asn Thr Gly Gly Lys Asp Gly Arg Val Ser Ile Glu Val Asp Pro
            100                 105                 110

Arg Leu Ala His Asn Thr His Ala Thr Val Ala Glu Ala Lys Gln Leu
        115                 120                 125

Ala Trp Leu Val Asp Arg Pro Asn Thr Phe Ile Lys Ile Pro Ala Thr
```

```
            130                 135                 140
Glu Ala Gly Leu Pro Ala Ile Ala Glu Thr Ile Gly Leu Gly Ile Ser
145                 150                 155                 160

Val Asn Val Thr Leu Ile Phe Ser Leu Glu Arg Tyr Arg Lys Val Met
                165                 170                 175

Asp Ala Phe Leu Thr Gly Leu Glu Lys Ala Lys Glu Arg Gly Leu Asp
                180                 185                 190

Leu Ser Gln Ile His Ser Val Ala Ser Phe Phe Val Ser Arg Val Asp
                195                 200                 205

Thr Glu Ile Asp Lys Arg Ile Asp Ala Leu Gly Thr Asp Glu Ala Lys
                210                 215                 220

Ala Gln Arg Gly Lys Ala Val Ala Asn Ala Arg Leu Ala Tyr Gln
225                 230                 235                 240

Ala Tyr Glu Glu Val Phe Gly Thr Asp Arg Trp Ala Ala Leu Glu Lys
                245                 250                 255

Ala Gly Ala Asn Lys Gln Arg Pro Leu Trp Ala Ser Thr Gly Val Lys
                260                 265                 270

Asp Lys Ala Tyr Ser Asp Thr Met Tyr Val Thr Asp Leu Val Ala Pro
                275                 280                 285

Asn Thr Val Asn Thr Met Pro Glu Ala Thr Leu Leu Ala Thr Glu Asp
                290                 295                 300

His Gly Glu Ile Thr Gly Asp Ala Val Ala Gly Ser Tyr Glu Arg Ala
305                 310                 315                 320

Arg Ala Asp Leu Asp Ala Ile Glu Lys Leu Gly Ile Ser Tyr Asp Glu
                325                 330                 335

Val Val Gln Leu Leu Glu Lys Glu Gly Val Asp Lys Phe Glu Asp Ala
                340                 345                 350

Trp Asn Asp Leu Leu Lys Ser Thr Glu Ala Glu Leu Lys Arg Leu Ala
                355                 360                 365

Pro Ser Lys Gly
    370

<210> SEQ ID NO 2
<211> LENGTH: 381
<212> TYPE: PRT
<213> ORGANISM: Streptomyces lividans

<400> SEQUENCE: 2

Met Ile Thr Val Thr Glu Ala Thr Ala Thr Gly Ala Leu Gln Arg
1               5                   10                  15

Leu Ala Asp Gln Gly Val Ser Val Trp Leu Asp Asp Leu Ser Arg Arg
                20                  25                  30

Arg Ile Glu Ser Gly Asn Leu Ala Glu Leu Ile Arg Thr Lys Asn Val
                35                  40                  45

Val Gly Val Thr Thr Asn Pro Ser Ile Phe Gln Ala Ala Ile Gly Ser
                50                  55                  60

Gly Glu Gly Tyr Glu Glu Gln Leu Ala Asp Leu Ala Thr Arg Gly Val
65                  70                  75                  80

Thr Val Asp Glu Ala Val Arg Met Met Thr Thr Ala Asp Val Arg Ala
                85                  90                  95

Ala Ala Asp Val Leu Arg Gly Val Tyr Asp Ala Ser Gly Gly Arg Asp
                100                 105                 110

Gly Arg Val Ser Ile Glu Val Asp Pro Arg Leu Ala His Asp Thr Ala
                115                 120                 125
```

```
Ala Thr Val Ala Glu Ala Arg Gln Leu Ser Trp Leu Val Asp Arg Pro
    130                 135                 140

Asn Val Met Ile Lys Ile Pro Ala Thr Lys Ala Gly Leu Pro Ala Ile
145                 150                 155                 160

Thr Glu Val Ile Gly Ala Gly Ile Ser Val Asn Val Thr Leu Ile Phe
                165                 170                 175

Ser Leu Glu Arg Tyr Arg Glu Val Met Asp Ala Tyr Leu Ala Gly Leu
                180                 185                 190

Glu Lys Ala Gln Ala Ala Gly Ile Asp Leu Ala Gly Ile His Ser Val
                195                 200                 205

Ala Ser Phe Phe Val Ser Arg Val Asp Ser Glu Ile Asp Lys Arg Leu
    210                 215                 220

Ser Leu Leu Gly Thr Glu Glu Ala Leu Gly Leu Arg Gly Arg Ala Ala
225                 230                 235                 240

Leu Ala Asn Ala Arg Leu Ala Tyr Glu Ala Tyr Glu Asn Val Phe Ala
                245                 250                 255

Gly Asp Arg Phe Thr Ala Leu Ala Gly Ala Arg Ala Asn Pro Gln Arg
                260                 265                 270

Pro Leu Trp Ala Ser Thr Gly Val Lys Asp Pro Ala Phe Arg Asp Thr
                275                 280                 285

Leu Tyr Val Glu Glu Leu Val Ala Pro Gly Thr Val Asn Thr Met Pro
    290                 295                 300

Glu Ala Thr Leu Asp Ala Ala Asp His Gly Asp Val Arg Gly Asp
305                 310                 315                 320

Thr Val Thr Gly Gly Tyr Ala Gln Ala Arg Ala Asp Leu Ala Ala Val
                325                 330                 335

Glu Arg Leu Gly Val Ser Tyr Asp Glu Val Val Glu Gln Leu Glu Gln
                340                 345                 350

Glu Gly Val Ala Lys Phe Glu Ala Ala Trp Gln Glu Leu Leu Ala Ala
                355                 360                 365

Val Thr Lys Ser Leu Asp Ser Lys Gly Val Asp Gly Glu
    370                 375                 380

<210> SEQ ID NO 3
<211> LENGTH: 372
<212> TYPE: PRT
<213> ORGANISM: Streptomyces avermitilis

<400> SEQUENCE: 3

Met Thr Asp Ala Leu Lys Arg Leu Ser Lys Glu Gly Val Ala Ile Trp
1               5                   10                  15

Leu Asp Asp Leu Ser Arg Lys Arg Ile Thr Ser Gly Asn Leu Ala Glu
                20                  25                  30

Leu Ile Asp Gln Gln His Val Val Gly Val Thr Thr Asn Pro Ser Ile
            35                  40                  45

Phe Gln Lys Ala Ile Ser Gln Gly Asp Gly Tyr Asp Gln Gln Val Ser
        50                  55                  60

Asp Leu Ala Ala Arg Arg Val Thr Val Glu Glu Ala Ile Arg Met Ile
65              70                  75                  80

Thr Thr Ala Asp Val Arg Asp Ala Ala Asp Ile Leu Arg Pro Val Phe
                85                  90                  95

Asp Ala Thr Asp Gly Gln Asp Gly Arg Val Ser Ile Glu Val Asp Pro
                100                 105                 110

Arg Leu Ala His Asn Thr Lys Ala Thr Val Ala Glu Ala Lys Gln Leu
            115                 120                 125
```

Ala Trp Leu Val Asp Arg Pro Asn Thr Leu Ile Lys Ile Pro Ala Thr
130                 135                 140

Lys Ala Gly Ile Pro Ala Ile Thr Glu Val Ile Gly Leu Gly Ile Ser
145                 150                 155                 160

Val Asn Val Thr Leu Ile Phe Ser Leu Glu Arg Tyr Arg Met Val Met
                165                 170                 175

Asp Ala Tyr Leu Ala Gly Leu Glu Lys Ala Lys Glu Arg Gly Leu Asp
                180                 185                 190

Leu Ser Lys Ile His Ser Val Ala Ser Phe Phe Val Ser Arg Val Asp
        195                 200                 205

Thr Glu Ile Asp Lys Arg Ile Asp Ala Leu Gly Thr Pro Glu Ala Lys
210                 215                 220

Ala Ala Arg Gly Lys Ala Gly Leu Ala Asn Ala Arg Leu Ala Tyr Glu
225                 230                 235                 240

Ala Tyr Glu Ala Val Phe Ser Thr Asp Arg Trp Leu Ala Leu Asp Lys
                245                 250                 255

Ala Gln Ala Asn Lys Gln Arg Pro Leu Trp Ala Ser Thr Gly Val Lys
                260                 265                 270

Asp Pro Ala Tyr Lys Asp Thr Met Tyr Val Glu Glu Leu Val Ala Pro
        275                 280                 285

Asn Thr Val Asn Thr Met Pro Glu Ala Thr Leu Glu Ala Thr Ala Asp
290                 295                 300

His Gly Glu Ile Arg Gly Asn Thr Ile Ala Gly Thr Tyr Glu Gln Ala
305                 310                 315                 320

Arg Ala Asp Leu Asp Ala Val Glu Lys Leu Gly Ile Ala Tyr Asp Asp
                325                 330                 335

Val Val Gln Leu Leu Glu Glu Glu Gly Val Asp Lys Phe Glu Ala Ser
                340                 345                 350

Trp Asn Asp Leu Leu Lys Ser Thr Glu Ala Glu Leu Gln Arg Leu Ala
        355                 360                 365

Pro Ser Glu Gly
        370

<210> SEQ ID NO 4
<211> LENGTH: 378
<212> TYPE: PRT
<213> ORGANISM: Streptomyces avermitilis

<400> SEQUENCE: 4

Met Ile Thr Val Ser Asn Thr Val Glu Asn Leu Glu Arg Leu Ser Asp
1               5                   10                  15

Glu Gly Val Ser Ile Trp Leu Asp Asp Leu Ser Arg Lys Arg Ile Thr
                20                  25                  30

Ser Gly Asn Leu Ala Glu Leu Ile Ala His Lys His Val Val Gly Val
                35                  40                  45

Thr Thr Asn Pro Ser Ile Phe Gln Ala Ala Ile Gly Ser Gly Glu Gly
        50                  55                  60

Tyr Glu Glu Gln Leu Ala Asp Leu Ala Val Arg Gly Val Thr Val Asp
65              70                  75                  80

Glu Ala Val Arg Met Met Thr Thr Ala Asp Val Arg Ala Ala Ala Asp
                85                  90                  95

Ile Leu Arg Pro Val Tyr Asp Ala Thr Gly Gly Arg Asp Gly Arg Val
                100                 105                 110

Ser Ile Glu Val Asp Pro Arg Leu Ala His Asp Thr Glu Ala Thr Ile

```
            115                 120                 125
Ala Glu Ala Lys Gln Leu Ala Trp Leu Val Asp Arg Pro Asn Val Met
        130                 135                 140

Ile Lys Ile Pro Ala Thr Lys Ala Gly Leu Pro Ala Ile Thr Glu Val
145                 150                 155                 160

Ile Gly Leu Gly Ile Ser Val Asn Val Thr Leu Ile Phe Ser Leu Glu
                165                 170                 175

Arg Tyr Arg Glu Val Met Asp Ala Tyr Leu Ala Gly Leu Glu Arg Ala
            180                 185                 190

Gln Ala Ala Gly Ile Asp Leu Ala Gly Ile His Ser Val Ala Ser Phe
        195                 200                 205

Phe Val Ser Arg Val Asp Ser Glu Ile Asp Lys Arg Leu Ala Lys Ala
        210                 215                 220

Gly Thr Asp Asp Ala Gln Ala Leu Lys Gly Lys Ala Ala Leu Ala Asn
225                 230                 235                 240

Ala Arg Leu Ala Tyr Glu Ala Tyr Glu Val Phe Ala Gly Glu Arg
                245                 250                 255

Trp Thr Ala Leu Ala Pro Ala Gly Ala His Lys Gln Arg Pro Leu Trp
            260                 265                 270

Ala Ser Thr Gly Val Lys Asp Pro Ala Tyr Lys Asp Thr Leu Tyr Val
            275                 280                 285

Asp Glu Leu Val Ala Pro Gly Thr Val Asn Thr Met Pro Glu Gly Thr
        290                 295                 300

Leu Asn Ala Thr Ala Asp His Gly Asp Ile His Gly Asp Thr Val Thr
305                 310                 315                 320

Gly Gly Tyr Ala Gln Ala Arg Ala Asp Leu Ala Ala Val Glu Arg Leu
                325                 330                 335

Gly Ile Ser Tyr Asp Glu Val Val Lys Gln Leu Glu Asp Glu Ala Val
            340                 345                 350

Ala Lys Phe Glu Val Ala Trp Gly Asp Leu Leu Glu Ala Val Ala Thr
        355                 360                 365

Ser Leu Arg Gly Lys Gly Ala Asp Gly Glu
    370                 375

<210> SEQ ID NO 5
<211> LENGTH: 530
<212> TYPE: PRT
<213> ORGANISM: Streptomyces lividans

<400> SEQUENCE: 5

Met Ser Glu Pro Glu Glu Gln Gln Pro Asp Ile His Thr Thr Ala Gly
1               5                   10                  15

Lys Leu Ala Asp Leu Arg Arg Ile Glu Glu Ala Thr His Ala Gly
            20                  25                  30

Ser Ala Arg Ala Val Glu Lys Gln His Ala Lys Gly Lys Leu Thr Ala
        35                  40                  45

Arg Glu Arg Ile Asp Leu Leu Asp Glu Gly Ser Phe Val Glu Leu
    50                  55                  60

Asp Glu Phe Ala Arg His Arg Ser Thr Asn Phe Gly Leu Asp Ala Asn
65                  70                  75                  80

Arg Pro Tyr Gly Asp Gly Val Val Thr Gly Tyr Gly Thr Val Asp Gly
                85                  90                  95

Arg Pro Val Ala Val Phe Ser Gln Asp Phe Thr Val Phe Gly Gly Ala
            100                 105                 110
```

```
Leu Gly Glu Val Tyr Gly Gln Lys Ile Val Lys Val Met Asp Phe Ala
            115                 120                 125

Leu Lys Thr Gly Cys Pro Val Gly Ile Asn Asp Ser Gly Gly Ala
130                 135                 140

Arg Ile Gln Glu Gly Val Ala Ser Leu Gly Ala Tyr Gly Glu Ile Phe
145                 150                 155                 160

Arg Arg Asn Thr His Ala Ser Gly Val Ile Pro Gln Ile Ser Leu Val
                165                 170                 175

Val Gly Pro Cys Ala Gly Gly Ala Val Tyr Ser Pro Ala Ile Thr Asp
            180                 185                 190

Phe Thr Val Met Val Asp Gln Thr Ser His Met Phe Ile Thr Gly Pro
                195                 200                 205

Asp Val Ile Lys Thr Val Thr Gly Glu Asp Val Gly Phe Glu Glu Leu
210                 215                 220

Gly Gly Ala Arg Thr His Asn Thr Ala Ser Gly Val Ala His His Met
225                 230                 235                 240

Ala Gly Asp Glu Lys Asp Ala Val Glu Tyr Val Lys Gln Leu Leu Ser
                245                 250                 255

Tyr Leu Pro Ser Asn Asn Leu Ser Glu Pro Ala Phe Pro Glu Glu
            260                 265                 270

Ala Asp Leu Ala Val Thr Asp Glu Asp Ala Glu Leu Asp Ala Ile Val
            275                 280                 285

Pro Asp Ser Ala Asn Gln Pro Tyr Asp Met His Ser Val Ile Glu His
            290                 295                 300

Val Leu Asp Asp Gly Glu Phe Phe Glu Thr Gln Pro Leu Phe Ala Pro
305                 310                 315                 320

Asn Ile Leu Thr Gly Phe Gly Arg Val Glu Gly Arg Pro Val Gly Ile
                325                 330                 335

Val Ala Asn Gln Pro Met Gln Phe Ala Gly Cys Leu Asp Ile Thr Ala
            340                 345                 350

Ser Glu Lys Ala Ala Arg Phe Val Arg Thr Cys Asp Ala Phe Asn Val
            355                 360                 365

Pro Val Leu Thr Phe Val Asp Val Pro Gly Phe Leu Pro Gly Val Asp
            370                 375                 380

Gln Glu His Asp Gly Ile Ile Arg Arg Gly Ala Lys Leu Ile Phe Ala
385                 390                 395                 400

Tyr Ala Glu Ala Thr Val Pro Leu Ile Thr Val Ile Thr Arg Lys Ala
                405                 410                 415

Phe Gly Gly Ala Tyr Asp Val Met Gly Ser Lys His Leu Gly Ala Asp
                420                 425                 430

Leu Asn Leu Ala Trp Pro Thr Ala Gln Ile Ala Val Met Gly Ala Gln
            435                 440                 445

Gly Ala Val Asn Ile Leu His Arg Arg Thr Ile Ala Asp Ala Gly Asp
450                 455                 460

Asp Ala Glu Ala Thr Arg Ala Arg Leu Ile Gln Glu Tyr Glu Asp Ala
465                 470                 475                 480

Leu Leu Asn Pro Tyr Thr Ala Ala Glu Arg Gly Tyr Val Asp Ala Val
                485                 490                 495

Ile Met Pro Ser Asp Thr Arg Arg His Ile Val Arg Gly Leu Arg Gln
            500                 505                 510

Leu Arg Thr Lys Arg Glu Ser Leu Pro Pro Lys Lys His Gly Asn Ile
            515                 520                 525

Pro Leu
```

<210> SEQ ID NO 6
<211> LENGTH: 532
<212> TYPE: PRT
<213> ORGANISM: Streptomyces avermitilis

<400> SEQUENCE: 6

```
Met Ser Glu Pro Glu Leu His His Pro Asp Ile His Thr Thr Ala
1               5                   10                  15

Gly Lys Leu Ala Asp Leu Gln Arg Arg Ile Gln Glu Ala Thr His Ala
            20                  25                  30

Gly Ser Glu Arg Ala Val Glu Lys Gln His Ala Lys Gly Lys Leu Thr
        35                  40                  45

Ala Arg Glu Arg Ile Ala Leu Leu Asp Glu Asp Ser Phe Val Glu
    50                  55                  60

Leu Asp Glu Phe Ala Gln His Arg Ser Thr Asp Phe Gly Met Glu Asn
65                  70                  75                  80

Asn Arg Pro Tyr Gly Asp Gly Val Val Thr Gly Tyr Gly Thr Val Asp
                85                  90                  95

Gly Arg Pro Val Ala Val Phe Ser Gln Asp Phe Thr Val Phe Gly Gly
            100                 105                 110

Ala Leu Gly Glu Val Phe Gly Gln Lys Ile Met Lys Ala Met Asp Phe
        115                 120                 125

Ala Leu Lys Thr Gly Cys Pro Val Ile Gly Ile Asn Asp Ser Gly Gly
    130                 135                 140

Ala Arg Ile Gln Glu Gly Val Ser Ala Leu Gly Met Tyr Gly Glu Ile
145                 150                 155                 160

Phe Arg Arg Asn Thr His Ala Ser Gly Val Ile Pro Gln Ile Ser Leu
                165                 170                 175

Val Val Gly Pro Cys Ala Gly Gly Ala Val Tyr Ser Pro Ala Ile Thr
            180                 185                 190

Asp Phe Thr Val Met Val Asp Gln Thr Ser His Met Phe Ile Thr Gly
        195                 200                 205

Pro Asp Val Ile Lys Thr Val Thr Gly Glu Asp Val Gly Phe Glu Glu
    210                 215                 220

Leu Gly Gly Ala Arg Thr His Asn Ala Val Ser Gly Val Ala His His
225                 230                 235                 240

Met Ala Gly Glu Glu Lys Asp Ala Ile Glu Tyr Val Lys Gln Leu Leu
                245                 250                 255

Ser Tyr Leu Pro Ser Asn Asn Leu Ser Glu Pro Pro Ala Phe Pro Glu
            260                 265                 270

Glu Ala Asp Leu Ala Leu Thr Asp Glu Asp Arg Glu Leu Asp Thr Leu
        275                 280                 285

Val Pro Asp Ser Ala Asn Gln Pro Tyr Asp Met His Thr Val Ile Glu
    290                 295                 300

His Ile Leu Asp Asp Ala Glu Phe Leu Glu Thr Gln Pro Leu Phe Ala
305                 310                 315                 320

Pro Asn Ile Leu Thr Gly Phe Gly Arg Val Glu Gly His Pro Val Gly
                325                 330                 335

Ile Val Ala Asn Gln Pro Met Gln Phe Ala Gly Cys Leu Asp Ile Asp
            340                 345                 350

Ala Ser Glu Lys Ala Ala Arg Phe Val Arg Thr Cys Asp Ala Phe Asn
        355                 360                 365
```

```
Val Pro Val Ile Thr Phe Val Asp Val Pro Gly Phe Leu Pro Gly Val
        370                 375                 380

Gly Gln Glu His Asp Gly Ile Ile Arg Arg Gly Ala Lys Leu Ile Tyr
385                 390                 395                 400

Ala Tyr Ala Glu Ala Thr Val Pro Leu Ile Thr Val Ile Thr Arg Lys
                405                 410                 415

Ala Phe Gly Gly Ala Tyr Asp Val Met Gly Ser Lys His Leu Gly Ala
                420                 425                 430

Asp Leu Asn Leu Ala Trp Pro Thr Ala Gln Ile Ala Val Met Gly Ala
            435                 440                 445

Gln Gly Ala Val Asn Ile Leu His Arg Arg Thr Ile Ala Ala Thr Pro
450                 455                 460

Glu Glu Glu Arg Glu Glu Val Arg Arg Leu Ile Gln Glu Tyr Glu
465                 470                 475                 480

Asp Thr Leu Leu Asn Pro Tyr Thr Ala Ala Glu Arg Gly Tyr Ile Asp
                485                 490                 495

Gly Val Ile Met Pro Ser Asp Thr Arg Ala His Val Val Arg Gly Leu
                500                 505                 510

Arg Gln Leu Arg Thr Lys Arg Glu Ser Leu Pro Pro Lys Lys His Gly
            515                 520                 525

Asn Ile Pro Leu
        530

<210> SEQ ID NO 7
<211> LENGTH: 572
<212> TYPE: PRT
<213> ORGANISM: Streptomyces lividans

<400> SEQUENCE: 7

Met Thr Val Asn Glu Pro Val Pro Asp Thr Phe Glu Asp Thr Pro Ala
1               5                   10                  15

Gly Asp Arg His Pro Asp Trp Phe Lys Arg Ala Val Phe Tyr Glu Val
            20                  25                  30

Leu Val Arg Ser Phe Gln Asp Ser Asn Gly Asp Gly Ile Gly Asp Leu
        35                  40                  45

Lys Gly Leu Thr Ala Lys Leu Asp Tyr Leu Gln Trp Leu Gly Val Asp
50                  55                  60

Cys Leu Trp Leu Pro Pro Phe Phe Lys Ser Pro Leu Arg Asp Gly Gly
65                  70                  75                  80

Tyr Asp Val Ser Asp Tyr Thr Ala Val Leu Pro Glu Phe Gly Asp Leu
                85                  90                  95

Ala Asp Phe Val Glu Phe Val Asp Ala Ala His Gln Arg Gly Met Arg
                100                 105                 110

Val Ile Ile Asp Phe Val Met Asn His Thr Ser Asp Gln His Pro Trp
            115                 120                 125

Phe Gln Glu Ser Arg Lys Asn Pro Asp Gly Pro Tyr Gly Asp Tyr Tyr
        130                 135                 140

Val Trp Ala Asp Asp Thr Arg Tyr Ala Asp Ala Arg Ile Ile Phe
145                 150                 155                 160

Val Asp Thr Glu Ala Ser Asn Trp Thr Tyr Asp Pro Val Arg Gly Gln
                165                 170                 175

Tyr Tyr Trp His Arg Phe Phe Ser His Gln Pro Asp Leu Asn Tyr Glu
                180                 185                 190

Asn Pro Ala Val Gln Glu Glu Met Leu Ala Ala Leu Lys Phe Trp Leu
            195                 200                 205
```

Asp Leu Gly Val Asp Gly Tyr Arg Leu Asp Ala Val Pro Tyr Leu Tyr
        210                 215                 220

Ala Glu Glu Gly Thr Asn Cys Glu Asn Leu Pro Ala Ser His Ala Phe
225                 230                 235                 240

Leu Lys Arg Val Arg Arg Glu Ile Asp Ala Gln Tyr Pro Asp Thr Val
                245                 250                 255

Leu Leu Ala Glu Ala Asn Gln Trp Pro Glu Asp Val Val Asp Tyr Phe
            260                 265                 270

Gly Asp Tyr Ser Thr Gly Gly Asp Glu Cys His Met Ala Phe His Phe
        275                 280                 285

Pro Val Met Pro Arg Ile Phe Met Ala Val Arg Arg Glu Ser Arg Tyr
    290                 295                 300

Pro Val Ser Glu Ile Leu Ala Lys Thr Pro Ala Ile Pro Ser Gly Cys
305                 310                 315                 320

Gln Trp Gly Ile Phe Leu Arg Asn His Asp Glu Leu Thr Leu Glu Met
                325                 330                 335

Val Thr Asp Glu Glu Arg Asp Tyr Met Tyr Ala Glu Tyr Ala Lys Asp
            340                 345                 350

Pro Arg Met Arg Ala Asn Ile Gly Ile Arg Arg Leu Ala Thr Leu
        355                 360                 365

Leu Asp Asn Asp Arg Asp Gln Ile Glu Leu Phe Thr Ala Leu Leu Leu
    370                 375                 380

Ala Leu Pro Gly Ser Pro Ile Leu Tyr Tyr Gly Asp Glu Ile Gly Met
385                 390                 395                 400

Gly Asp Asn Ile Trp Leu Gly Asp Arg Asp Ala Val Arg Thr Pro Met
                405                 410                 415

Gln Trp Thr Pro Asp Arg Asn Ala Gly Phe Ser Thr Cys Asp Pro Gly
            420                 425                 430

Arg Leu Tyr Leu Pro Ala Ile Met Asp Pro Val Tyr Gly Tyr Gln Val
        435                 440                 445

Thr Asn Val Glu Ala Ser Met Ala Ser Pro Ser Ser Leu Leu His Trp
    450                 455                 460

Thr Arg Arg Met Ile Glu Ile Arg Lys Gln Asn Pro Ala Phe Gly Leu
465                 470                 475                 480

Gly Thr Tyr Thr Glu Leu Pro Ser Ser Asn Pro Ala Val Leu Ala Phe
                485                 490                 495

Leu Arg Glu Tyr Glu Asp Asp Leu Val Leu Cys Val Asn Asn Phe Ala
            500                 505                 510

Arg Phe Ala Gln Pro Thr Glu Leu Asp Leu Arg Glu Phe Ala Gly Arg
        515                 520                 525

His Pro Val Glu Leu Phe Gly Gly Val Arg Phe Pro Ala Ile Gly Glu
    530                 535                 540

Leu Pro Tyr Leu Leu Thr Leu Gly Gly His Gly Phe Tyr Trp Phe Arg
545                 550                 555                 560

Leu Thr Arg Val Ala Ser Arg Ile Gly Arg Arg Ala
                565                 570

<210> SEQ ID NO 8
<211> LENGTH: 583
<212> TYPE: PRT
<213> ORGANISM: Streptomyces avermitilis

<400> SEQUENCE: 8

Met Ile Val Asn Glu Pro Val Pro Asp Thr Phe Glu Asp Thr Pro Ala

```
1               5                   10                  15
Lys Asp Arg Asp Pro Glu Trp Phe Lys Arg Ala Val Phe Tyr Glu Val
                20                  25                  30
Leu Val Arg Ser Phe Gln Asp Ser Asn Gly Asp Gly Val Gly Asp Leu
                35                  40                  45
Lys Gly Leu Thr Ala Lys Leu Asp Tyr Leu Gln Trp Leu Gly Val Asp
                50                  55                  60
Cys Leu Trp Leu Pro Pro Phe Phe Lys Ser Pro Leu Arg Asp Gly Gly
65                  70                  75                  80
Tyr Asp Val Ser Asp Tyr Thr Ala Val Leu Pro Glu Phe Gly Asp Leu
                85                  90                  95
Ala Asp Phe Val Glu Phe Val Asp Ala Ala His Gln Arg Gly Met Arg
                100                 105                 110
Val Ile Ile Asp Phe Val Met Asn His Thr Ser Asp Leu His Pro Trp
                115                 120                 125
Phe Gln Glu Ser Arg Ser Asn Pro Asp Gly Pro Tyr Gly Asp Tyr Tyr
                130                 135                 140
Val Trp Ala Asp Asp Lys Gln Tyr Gln Asp Ala Arg Ile Ile Phe
145                 150                 155                 160
Val Asp Thr Glu Ala Ser Asn Trp Thr Tyr Asp Pro Val Arg Lys Gln
                165                 170                 175
Tyr Tyr Trp His Arg Phe Phe Ser His Gln Pro Asp Leu Asn Tyr Glu
                180                 185                 190
Ser Ala Ala Val Gln Glu Glu Ile Leu Ala Ala Leu Arg Phe Trp Leu
                195                 200                 205
Asp Leu Gly Ile Asp Gly Phe Arg Leu Asp Ala Val Pro Tyr Leu Tyr
                210                 215                 220
Asn Glu Glu Gly Thr Asn Cys Glu Asn Leu Pro Ala Thr His Glu Phe
225                 230                 235                 240
Leu Lys Arg Val Arg Lys Glu Ile Asp Thr His Tyr Pro Asp Thr Val
                245                 250                 255
Leu Leu Ala Glu Ala Asn Gln Trp Pro Glu Asp Val Val Asp Tyr Phe
                260                 265                 270
Gly Asp Phe Pro Ser Gly Gly Asp Glu Cys His Met Ala Phe His Phe
                275                 280                 285
Pro Val Met Pro Arg Ile Phe Met Ala Val Arg Arg Glu Ser Arg Tyr
                290                 295                 300
Pro Val Ser Glu Ile Leu Ala Lys Thr Pro Ala Ile Pro Ser Ser Cys
305                 310                 315                 320
Gln Trp Gly Ile Phe Leu Arg Asn His Asp Glu Leu Thr Leu Glu Met
                325                 330                 335
Val Thr Asp Glu Glu Arg Asp Tyr Met Trp Ala Glu Tyr Ala Lys Asp
                340                 345                 350
Pro Arg Met Arg Ala Asn Ile Gly Ile Arg Arg Leu Ala Pro Leu
                355                 360                 365
Leu Asp Asn Asp Arg Asn Gln Ile Glu Leu Phe Thr Ala Leu Leu Leu
370                 375                 380
Ser Leu Pro Gly Ser Pro Ile Leu Tyr Tyr Gly Asp Glu Ile Gly Met
385                 390                 395                 400
Gly Asp Asn Ile Trp Leu Gly Asp Arg Asp Ala Val Arg Thr Pro Met
                405                 410                 415
Gln Trp Thr Pro Asp Arg Asn Ala Gly Phe Ser Ser Cys Asp Pro Gly
                420                 425                 430
```

```
Arg Leu Tyr Leu Pro Thr Ile Met Asp Pro Val Tyr Gly Tyr Gln Val
            435                 440                 445

Thr Asn Val Glu Ala Ser Met Ser Ser Pro Ser Ser Leu Leu His Trp
    450                 455                 460

Thr Arg Arg Met Ile Glu Ile Arg Lys Gln Asn Pro Ala Phe Gly Leu
465                 470                 475                 480

Gly Ser Tyr Thr Glu Leu Gln Ser Ser Asn Pro Ala Val Leu Ala Phe
                485                 490                 495

Leu Arg Glu Ala Pro Ser Thr Gly Gly Asn Gly Asp Asp Leu Val Leu
            500                 505                 510

Cys Val His Asn Phe Ser Arg Phe Ala Gln Pro Thr Glu Leu Asp Leu
        515                 520                 525

Arg Ala Phe Ser Gly Arg His Pro Val Glu Leu Ile Gly Gly Val Arg
    530                 535                 540

Phe Pro Ala Ile Gly Glu Leu Pro Tyr Leu Thr Leu Ala Gly His
545                 550                 555                 560

Gly Phe Tyr Trp Phe Arg Leu Arg Lys Asp Val Thr Gln Val Thr Lys
                565                 570                 575

Val Ser Leu Phe Val Ser Ser
            580

<210> SEQ ID NO 9
<211> LENGTH: 566
<212> TYPE: PRT
<213> ORGANISM: Streptomyces lividans

<400> SEQUENCE: 9

Met Thr Val Asn Glu Pro Val Pro Asp Thr Phe Glu Asp Thr Pro Ala
1               5                   10                  15

Gly Asp Arg His Pro Asp Trp Phe Lys Arg Ala Val Phe Tyr Glu Val
            20                  25                  30

Leu Val Arg Ser Phe Gln Asp Ser Asn Gly Asp Gly Ile Gly Asp Leu
        35                  40                  45

Lys Gly Leu Thr Ala Lys Leu Asp Tyr Leu Gln Trp Leu Gly Val Asp
    50                  55                  60

Cys Leu Trp Leu Pro Pro Phe Phe Lys Ser Pro Leu Arg Asp Gly Gly
65                  70                  75                  80

Tyr Asp Val Ser Asp Tyr Thr Ala Val Leu Pro Glu Phe Gly Asp Leu
                85                  90                  95

Ala Asp Phe Val Glu Phe Val Asp Ala Ala His Gln Arg Gly Met Arg
            100                 105                 110

Val Ile Ile Asp Phe Val Met Asn His Thr Ser Asp Gln His Pro Trp
        115                 120                 125

Phe Gln Glu Ser Arg Arg Asn Pro Asp Gly Pro Tyr Gly Asp Tyr Tyr
    130                 135                 140

Val Trp Ala Asp Asp Lys Gln Phe Gln Asp Ala Arg Ile Ile Phe
145                 150                 155                 160

Val Asp Thr Glu Ala Ser Asn Trp Thr Tyr Asp Pro Val Arg Lys Gln
                165                 170                 175

Tyr Tyr Trp His Arg Phe Phe Ser His Gln Pro Asp Leu Asn Tyr Glu
            180                 185                 190

Asn Pro Val Val Gln Glu Glu Met Ile Ser Ala Leu Lys Phe Trp Leu
        195                 200                 205

Asp Leu Gly Ile Asp Gly Phe Arg Leu Asp Ala Val Pro Tyr Leu Tyr
```

```
                    210                 215                 220
Gln Glu Glu Gly Thr Asn Cys Glu Asn Leu Pro Arg Thr His Asp Phe
225                 230                 235                 240

Leu Lys Arg Val Arg Lys Glu Ile Asp Ala Gln Tyr Pro Asp Thr Val
                245                 250                 255

Val Leu Ala Glu Ala Asn Gln Trp Pro Glu Asp Val Val Asp Tyr Phe
            260                 265                 270

Gly Asp Tyr Ala Ala Gly Gly Asp Glu Cys His Met Ala Phe His Phe
        275                 280                 285

Pro Val Met Pro Arg Ile Phe Met Ala Val Arg Arg Glu Ser Arg Tyr
    290                 295                 300

Pro Val Ser Glu Ile Leu Ala Lys Thr Pro Ala Ile Pro Ser Gly Cys
305                 310                 315                 320

Gln Trp Gly Ile Phe Leu Arg Asn His Asp Glu Leu Thr Leu Glu Met
                325                 330                 335

Val Thr Asp Glu Glu Arg Asp Tyr Met Tyr Ala Glu Tyr Ala Lys Asp
                340                 345                 350

Pro Arg Met Arg Ala Asn Ile Gly Ile Arg Arg Arg Leu Ala Pro Leu
            355                 360                 365

Leu Asp Asn Asp Arg Asn Gln Ile Glu Leu Phe Thr Ala Leu Leu Leu
        370                 375                 380

Ser Leu Pro Gly Ser Pro Ile Leu Tyr Tyr Gly Asp Glu Ile Gly Met
385                 390                 395                 400

Gly Asp Asn Ile Trp Leu Gly Asp Arg Asp Ala Val Arg Thr Pro Met
                405                 410                 415

Gln Trp Thr Pro Asp Arg Asn Ala Gly Phe Ser Ser Asp Pro Gly
                420                 425                 430

Arg Leu Phe Leu Pro Thr Ile Met Asp Pro Val His Gly Tyr Gln Val
            435                 440                 445

Thr Asn Val Glu Ala Ser Met Ala Ser Pro Ser Ser Leu Leu His Trp
        450                 455                 460

Thr Arg Arg Met Ile Glu Ile Arg Lys Gln Asn Val Ala Phe Gly Leu
465                 470                 475                 480

Gly Thr Tyr Thr Glu Leu Pro Ser Ser Asn Pro Ala Val Leu Ala Phe
                485                 490                 495

Leu Arg Glu His Glu Asp Asp Leu Val Leu Cys Val His Asn Phe Ser
                500                 505                 510

Arg Phe Ala Gln Pro Thr Glu Leu Asp Leu Ser Ala Phe Asp Gly Arg
            515                 520                 525

His Pro Val Glu Leu Phe Gly Gly Val Arg Phe Pro Ala Val Gly Asp
        530                 535                 540

Leu Pro Tyr Leu Leu Thr Leu Gly Gly His Gly Phe Tyr Trp Phe Arg
545                 550                 555                 560

Leu Arg Lys Asp Ala Ala
                565

<210> SEQ ID NO 10
<211> LENGTH: 572
<212> TYPE: PRT
<213> ORGANISM: Streptomyces avermitilis

<400> SEQUENCE: 10

Met Ile Val Asn Glu Pro Val Pro Asp Thr Phe Glu Asp Thr Pro Ala
1               5                   10                  15
```

-continued

Lys Asp Arg Asp Pro Glu Trp Phe Lys Arg Ala Val Phe Tyr Glu Val
            20                  25                  30

Leu Val Arg Ser Phe Gln Asp Ser Asn Gly Asp Gly Val Gly Asp Leu
        35                  40                  45

Lys Gly Leu Thr Ala Lys Leu Asp Tyr Leu Gln Trp Leu Gly Val Asp
    50                  55                  60

Cys Leu Trp Leu Pro Pro Phe Phe Lys Ser Pro Leu Arg Asp Gly Gly
65                  70                  75                  80

Tyr Asp Val Ser Asp Tyr Thr Ala Val Leu Pro Glu Phe Gly Asp Leu
                85                  90                  95

Ala Asp Phe Val Glu Phe Val Asp Ala Ala His Gln Arg Gly Met Arg
                100                 105                 110

Val Ile Ile Asp Phe Val Met Asn His Thr Ser Asp Leu His Pro Trp
            115                 120                 125

Phe Gln Glu Ser Arg Ser Asn Pro Asp Gly Pro Tyr Gly Asp Tyr Tyr
        130                 135                 140

Val Trp Ala Asp Asp Lys Gln Tyr Gln Asp Ala Arg Ile Ile Phe
145                 150                 155                 160

Val Asp Thr Glu Ala Ser Asn Trp Thr Phe Asp Pro Val Arg Lys Gln
                165                 170                 175

Tyr Tyr Trp His Arg Phe Phe Ser His Gln Pro Asp Leu Asn Tyr Glu
                180                 185                 190

Asn Pro Ala Val Gln Glu Glu Ile Val Ser Ala Leu Arg Phe Trp Leu
            195                 200                 205

Asp Leu Gly Ile Asp Gly Phe Arg Leu Asp Ala Val Pro Tyr Leu Tyr
        210                 215                 220

Gln Gln Glu Gly Thr Asn Cys Glu Asn Leu Pro Ala Thr His Glu Phe
225                 230                 235                 240

Leu Lys Arg Val Arg Lys Glu Ile Asp Thr His Tyr Pro Asp Thr Val
                245                 250                 255

Leu Leu Ala Glu Ala Asn Gln Trp Pro Glu Asp Val Val Asp Tyr Phe
                260                 265                 270

Gly Asp Phe Pro Ser Gly Gly Asp Glu Cys His Met Ala Phe His Phe
            275                 280                 285

Pro Val Met Pro Arg Ile Phe Met Ala Val Arg Arg Glu Ser Arg Tyr
        290                 295                 300

Pro Val Ser Glu Ile Leu Ala Lys Thr Pro Ala Ile Pro Ser Ser Cys
305                 310                 315                 320

Gln Trp Gly Ile Phe Leu Arg Asn His Asp Glu Leu Thr Leu Glu Met
                325                 330                 335

Val Thr Asp Glu Glu Arg Asp Tyr Met Trp Ala Glu Tyr Ala Lys Asp
                340                 345                 350

Pro Arg Met Arg Ala Asn Ile Gly Ile Arg Arg Leu Ala Pro Leu
        355                 360                 365

Leu Asp Asn Asp Arg Asn Gln Ile Glu Leu Phe Thr Ala Leu Leu Leu
        370                 375                 380

Ser Leu Pro Gly Ser Pro Ile Leu Tyr Tyr Gly Asp Glu Ile Gly Met
385                 390                 395                 400

Gly Asp Asn Ile Trp Leu Gly Asp Arg Asp Ala Val Arg Thr Pro Met
                405                 410                 415

Gln Trp Thr Pro Asp Arg Asn Ala Gly Phe Ser Ser Cys Asp Pro Gly
                420                 425                 430

Arg Leu Tyr Leu Pro Thr Ile Met Asp Pro Val Tyr Gly Tyr Gln Val

```
            435                 440                 445
Thr Asn Val Glu Ala Ser Met Ser Pro Ser Ser Leu Leu His Trp
450                 455                 460

Thr Arg Arg Met Ile Glu Ile Arg Lys Gln Asn Pro Ala Phe Gly Leu
465                 470                 475                 480

Gly Ser Tyr Thr Glu Leu Gln Ser Ser Asn Pro Ala Val Leu Ala Phe
                    485                 490                 495

Leu Arg Glu Ala Pro Ser Thr Gly Gly Asn Gly Asp Asp Leu Val Leu
                500                 505                 510

Cys Val His Asn Phe Ser Arg Phe Ala Gln Pro Thr Glu Leu Asp Leu
                515                 520                 525

Arg Ala Phe Ser Gly Arg His Pro Val Glu Leu Ile Gly Gly Val Arg
                530                 535                 540

Phe Pro Ala Ile Gly Leu Pro Tyr Leu Leu Thr Leu Ala Gly His
545                 550                 555                 560

Gly Phe Tyr Trp Phe Arg Leu Arg Lys Asp Ala Val
                565                 570

<210> SEQ ID NO 11
<211> LENGTH: 704
<212> TYPE: PRT
<213> ORGANISM: Streptomyces lividans

<400> SEQUENCE: 11

Val Phe Met Gln Val Trp Pro Gly Glu Ala Tyr Pro Leu Gly Ala Thr
1               5                   10                  15

Tyr Asp Gly Ala Gly Thr Asn Phe Ala Val Phe Thr Glu Ala Ala Asp
                20                  25                  30

Arg Val Glu Leu Cys Leu Leu His Asp Asp Gly Ser Glu Thr Ala Val
            35                  40                  45

Glu Leu Arg Glu Ser Asp Ala Phe Val Arg His Ala Tyr Val Pro Gly
        50                  55                  60

Val Met Pro Gly Gln Arg Tyr Gly Tyr Arg Val His Gly Pro Tyr Ala
65                  70                  75                  80

Pro Glu Arg Gly Leu Arg Cys Asn Ser Ala Lys Leu Leu Leu Asp Pro
                85                  90                  95

Tyr Ala Arg Ala Ile Ser Gly Glu Val Gln Trp Gly Glu Glu Val Tyr
                100                 105                 110

Gly Tyr His Phe Gly Ala Pro Glu Arg Arg Asn Asp Leu Asp Ser Ala
            115                 120                 125

Pro His Thr Met Thr Ser Val Val Asn Pro Tyr Phe Asp Trp Gly
130                 135                 140

Asp Asp Arg Arg Pro Arg Thr Glu Tyr His His Thr Val Ile Tyr Glu
145                 150                 155                 160

Ala His Val Lys Gly Leu Thr Met Arg His Pro Gly Leu Pro Glu Glu
                165                 170                 175

Leu Arg Gly Thr Tyr Ala Ala Leu Ala His Pro Ala Leu Ile Glu His
                180                 185                 190

Leu Thr Gly Leu Gly Val Thr Ala Leu Glu Leu Met Pro Val His Gln
            195                 200                 205

Phe Val Asn Asp His Arg Leu Val Asp Met Gly Leu Asn Asn Tyr Trp
210                 215                 220

Gly Tyr Asn Thr Val Gly Phe Phe Ala Pro His Asn Ala Tyr Ala Ser
225                 230                 235                 240
```

-continued

```
Trp Gly Asp Arg Gly Gln Gln Val Leu Glu Phe Lys Ser Ala Val Lys
            245                 250                 255

Ala Leu His Glu Ala Gly Ile Glu Val Ile Leu Asp Val Val Tyr Asn
        260                 265                 270

His Thr Ala Glu Gly Asn His Leu Gly Pro Thr Leu Ser Phe Lys Gly
    275                 280                 285

Leu Asp Asn Pro Ser Tyr Tyr Arg Leu Ala Asp Pro Arg Tyr Tyr
290                 295                 300

Met Asp Thr Thr Gly Thr Gly Asn Ser Leu Leu Met Arg Ser Pro His
305                 310                 315                 320

Val Leu Gln Met Ile Met Asp Ser Leu Arg Tyr Trp Val Thr Glu Met
                325                 330                 335

His Val Asp Gly Phe Arg Phe Asp Leu Ala Ala Thr Leu Ala Arg Gln
            340                 345                 350

Phe His Glu Val Asp Arg Leu Ser Ser Phe Phe Asp Leu Val Gln Gln
        355                 360                 365

Asp Pro Val Val Ser Gln Val Lys Leu Ile Ala Glu Pro Trp Asp Val
    370                 375                 380

Gly Glu Gly Gly Tyr Gln Val Gly Asn Phe Pro Pro Leu Trp Thr Glu
385                 390                 395                 400

Trp Asn Gly Lys Tyr Arg Asp Thr Val Arg Asp Leu Trp Arg Gly Glu
                405                 410                 415

Pro Arg Thr Leu Ala Glu Phe Ala Ser Arg Leu Thr Gly Ser Ser Asp
            420                 425                 430

Leu Tyr Gln Asp Asp Gly Arg Arg Pro Leu Ala Ser Ile Asn Phe Val
        435                 440                 445

Thr Cys His Asp Gly Phe Thr Leu His Asp Met Val Ala Tyr Asn Asp
    450                 455                 460

Lys His Asn His Ala Asn Gly Glu Asp Asn Arg Asp Gly Glu Ser His
465                 470                 475                 480

Asn Arg Ser Trp Asn Cys Gly Val Glu Gly Asp Thr Asp Pro Ala
                485                 490                 495

Val Leu Glu Leu Arg Ala Arg Gln Met Arg Asn Phe Ile Ala Thr Leu
            500                 505                 510

Leu Leu Ser Gln Gly Val Pro Met Leu Ser His Gly Asp Glu Phe Ala
        515                 520                 525

Arg Thr Gln Arg Gly Asn Asn Asn Ala Tyr Cys Gln Asp Asn Glu Leu
    530                 535                 540

Ala Trp Val Ala Trp Pro Glu Asp Gly His Asp Leu Leu Glu Phe Thr
545                 550                 555                 560

Arg Ala Met Val Trp Leu Arg Lys Asp His Pro Val Leu Arg Arg Arg
                565                 570                 575

Arg Phe Phe His Gly Arg Pro Val Gln Gly Thr His Asp Glu Leu Ser
            580                 585                 590

Asp Ile Ala Trp Phe Thr Pro Glu Gly Ala Glu Met Ala Gln Arg Asp
        595                 600                 605

Trp Asn Ser Ala Arg Ala Ser Ala Leu Thr Val Phe Leu Asn Gly Asn
    610                 615                 620

Ala Ile Ser Glu Pro Gly Thr Arg Gly Glu Arg Ile Ala Asp Asp Ser
625                 630                 635                 640

Phe Leu Leu Met Phe Asn Ala Ala Pro Arg Pro Leu Asp Phe Val Val
                645                 650                 655

Pro Val Asp His Gly Arg Gln Trp Glu Val Val Val Asp Thr Ala Leu
```

```
                    660                 665                 670
Thr Ala Gly Val Pro Thr Gly Thr Gly Pro Lys Val Gln Ala Gly Asp
            675                 680                 685

Arg Leu Thr Leu Leu Asp Arg Ser Leu Thr Val Leu Gln Arg Pro Val
        690                 695                 700

<210> SEQ ID NO 12
<211> LENGTH: 702
<212> TYPE: PRT
<213> ORGANISM: Streptomyces avermitilis

<400> SEQUENCE: 12

Met Gln Val Trp Pro Gly Glu Ala Tyr Pro Leu Gly Ala Thr Tyr Asp
1               5                   10                  15

Gly Ala Gly Thr Asn Phe Ala Val Phe Ser Glu Ala Ala His Arg Ile
            20                  25                  30

Glu Leu Cys Leu Leu His Asp Asp Gly Ser Glu Thr Ala Val Glu Leu
        35                  40                  45

Arg Glu Thr Asp Ala Phe Val Arg His Ala Tyr Leu Pro Gly Val Met
    50                  55                  60

Pro Gly Gln Arg Tyr Gly Phe Arg Val His Gly Pro Phe Ala Pro Gly
65                  70                  75                  80

Arg Gly Val Arg Cys Asn Ser Ala Lys Leu Leu Leu Asp Pro Tyr Ala
                85                  90                  95

Lys Ala Ile Ser Gly Glu Ile Lys Trp Gly Glu Glu Val Tyr Gly Tyr
            100                 105                 110

His Phe Gly Ala Pro Asp Lys Arg Asn Asp Leu Asp Ser Ala Pro His
        115                 120                 125

Thr Met Thr Ser Val Val Ile Asn Pro Tyr Phe Asp Trp Gly Asn Asp
    130                 135                 140

Arg Arg Pro Arg Thr Glu Tyr His His Thr Val Leu Tyr Glu Ala His
145                 150                 155                 160

Val Lys Gly Leu Thr Met Arg His Pro Ala Leu Pro Glu Glu Leu Arg
                165                 170                 175

Gly Thr Tyr Ala Ala Leu Ala His Pro Ala Ile Ile Glu His Leu Thr
            180                 185                 190

Glu Leu Gly Val Thr Ala Leu Glu Leu Met Pro Val His Gln Phe Val
        195                 200                 205

Asn Asp His Arg Leu Val Asp Met Gly Leu Asn Asn Tyr Trp Gly Tyr
    210                 215                 220

Asn Thr Ile Gly Phe Phe Ala Pro His Asn Ala Tyr Ala Ser Trp Gly
225                 230                 235                 240

Asp Arg Gly Gln Gln Val Leu Glu Phe Lys Ser Ala Val Lys Ala Leu
                245                 250                 255

His Glu Ala Gly Ile Glu Val Ile Leu Asp Val Val Tyr Asn His Thr
            260                 265                 270

Ala Glu Gly Asn His Met Gly Pro Thr Leu Ser Phe Lys Gly Ile Asp
        275                 280                 285

Asn Ala Ser Tyr Tyr Arg Leu Thr Asp Asp Pro Arg Tyr Tyr Met Asp
    290                 295                 300

Thr Thr Gly Thr Gly Asn Ser Leu Leu Met Arg Ser Pro His Val Leu
305                 310                 315                 320

Gln Leu Ile Met Asp Ser Leu Arg Tyr Trp Val Ser Asp Met His Val
                325                 330                 335
```

```
Asp Gly Phe Arg Phe Asp Leu Ala Ala Thr Leu Ala Arg Gln Phe His
                340                 345                 350
Glu Val Asp Arg Leu Ser Ser Phe Phe Asp Leu Val Gln Gln Asp Pro
            355                 360                 365
Val Val Ser Gln Val Lys Leu Ile Ala Glu Pro Trp Asp Val Gly Glu
        370                 375                 380
Gly Gly Tyr Gln Val Gly Asn Phe Pro Pro Leu Trp Thr Glu Trp Asn
385                 390                 395                 400
Gly Lys Tyr Arg Asp Thr Val Arg Asp Met Trp Arg Gly Glu Pro Arg
                405                 410                 415
Thr Leu Ala Glu Phe Ala Ser Arg Leu Thr Gly Ser Ser Asp Leu Tyr
            420                 425                 430
Gln Asp Asp Gly Arg Arg Pro Leu Ala Ser Ile Asn Phe Val Thr Cys
        435                 440                 445
His Asp Gly Phe Thr Leu His Asp Leu Val Ala Tyr Asn Asp Lys His
    450                 455                 460
Asn Gln Ala Asn Gly Glu Asp Asn Arg Asp Gly Glu Ser His Asn Arg
465                 470                 475                 480
Ser Trp Asn Cys Gly Ala Glu Gly Asp Thr Asp Pro Ala Val Leu
                485                 490                 495
Ala Leu Arg Ala Arg Gln Met Arg Asn Phe Ile Ala Thr Leu Met Leu
            500                 505                 510
Ser Gln Gly Val Pro Met Leu Ser His Gly Asp Glu Phe Ala Arg Thr
        515                 520                 525
Gln Gly Gly Asn Asn Ala Tyr Cys Gln Asp Gly Glu Leu Ser Trp
    530                 535                 540
Val Ala Trp Pro Glu Asp Gly Ser Glu Leu Leu Glu Phe Thr Arg Ala
545                 550                 555                 560
Met Val Trp Leu Arg Arg Asp His Pro Val Phe Arg Arg Arg Phe
                565                 570                 575
Phe His Gly Arg Pro Val Glu Gly Thr His Asp Glu Leu Ser Asp Ile
            580                 585                 590
Val Trp Phe Thr Pro Thr Gly Glu Glu Met Ile Gln Arg Asp Trp Asp
        595                 600                 605
Ser Ala Gln Ala Arg Ala Leu Thr Val Phe Leu Asn Gly Thr Ala Ile
625                 630                 635                 640
Leu Met Phe Asn Ala Ser Pro Lys Ser Leu Glu Phe Val Val Pro Val
                645                 650                 655
Asp His Gly Arg Gln Trp Gln Val Val Asp Thr Ala Arg Thr Asp
            660                 665                 670
Gly Ile Pro Pro Gly Thr Val Ala Lys Val Lys Ala Gly Asp Arg Leu
        675                 680                 685
Thr Leu Val Asp Arg Ser Leu Thr Val Leu Gln Arg Pro Ala
    690                 695                 700

<210> SEQ ID NO 13
<211> LENGTH: 1119
<212> TYPE: DNA
<213> ORGANISM: Streptomyces lividans

<400> SEQUENCE: 13
atgacagacg cactcaagcg cctctccgat gaaggcgtgg cgatctggct ggacgacctg          60
```

-continued

```
tcgcgcaagc ggatcacgtc cggcaacctc gccgagctga tcgaccagca gcacgtcgtg    120
ggcgtcacca ccaacccgtc gatcttccag aaggccatct cgcagggcga cggctacgac    180
cagcagctcg ccgacctcgc cgtccgcgga gtcacggtcg aagaggccat ccgcatgatc    240
accacggcgg acgtccgcga cgccgccgac atcctgcgcc ccgtctacga caacaccggc    300
ggcaaggacg gccgggtctc catcgaggtg acccgcggc tggcgcacaa cacccacgcc     360
acggtggccg aggccaagca gctggcgtgg ctggtggacc ggccgaacac cttcatcaag    420
atcccggcga ccgaggcggg cctgccggcc atcgccgaga ccatcggcct gggcatcagc    480
gtcaacgtca cgctgatctt ctccctggag cgctaccgca aggtcatgga cgccttcctg    540
accggcctgg agaaggccaa ggagcgtggc ctggacctct cgcagatcca ctccgtggcg    600
tccttcttcg tgtcccgcgt ggacaccgag atcgacaagc ggatcgacgc gctcggcacc    660
gacgaggcca aggcgcagcg cggcaaggcc gccgtcgcca cgcccgcct ggcctaccag     720 gcgtacgagg aggtcttcgg caccgaccgc tgggccgccc tggagaaggc cggcgccaac    780
aagcagcgtc cgctgtgggc gtcgaccggt gtgaaggaca aggcgtacag cgacaccatg    840
tacgtcaccg acctggtcgc gccgaacacg tcaacacca tgccggaggc cacgctgctg      900
gccaccgagg accacggcga gatcaccggc gacgccgtcg ccgggtcgta cgagcgggcc    960
cgcgcggacc tcgacgcgat cgagaagctc gggatctcct acgacgaggt ggtccagctc   1020
ctggagaagg aaggcgtcga caagttcgag gacgcctgga cgacctgct gaagtccacg    1080 gaggcggagc tcaagcgcct cgctcccctcg aagggctga                          1119
```

<210> SEQ ID NO 14
<211> LENGTH: 1146
<212> TYPE: DNA
<213> ORGANISM: Streptomyces lividans

<400> SEQUENCE: 14

```
atgatcactg tgaccgaagc aaccgccacc gcgggagcac tgcagcgcct ggccgaccag     60
ggcgtgtccg tctggctcga cgacctgtcg cggcggcgga tcgagtccgg caacctcgcc   120
gagctgatca ggacgaagaa cgtcgtcgga gtcaccacca acccgtcgat cttccaggcc   180
gccataggct ccggcgaggg ctacgaggag cagctcgccg acctggcgac ccggggcgtc   240
accgtcgacg aggcggtccg catgatgacc accgccgatg tccgcgccgc cgccgacgtg   300
ctgcgcgggg tgtacgacgc ctccggcggg cgcgacggcc gcgtctccat cgaggtcgac   360
ccgcgcctgg cccacgacac ggcggcgacg gtcgccgagg cccgccagct gtcctggctg    420
gtcgaccgtc ccaacgtgat gatcaagatc ccggcgacga aggccggtct cccggccatc    480
accgaggtca tcggcgccgg catcagtgtg aacgtcacgc tgatcttctc cctggagcgc    540
taccgcgagg tcatggacgc ctacctcgcc ggcctggaga aggcgcaggc ggccgggatc    600
gacctggccg gcatccactc ggtcgcgtcc ttcttcgtct cccgcgtcga cagcgagatc    660
gacaagcgcc tgtccctgct gggcaccgaa gaggcgctcg gcctgcgcgg ccgggcggca    720
ctggccaacg cacgactggc ctacgaggcg tacgagaacg tcttcgcggg cgaccgcttc    780
accgccctcg cggggcccg cgcgaacccc cagcgccccc tgtgggcgtc caccggtgtg    840
aaggacccgg cattccggga caccctgtac gtggaggagc tggtcgcccc cggcaccgtg    900
aacacgatgc cggaggccac cctggacgcc gccgccgatc acggcgacgt acggggcgac    960
acggtcaccg gcgggtacgc ccaggcccgc gccgatctcg cggccgtgga gcggctcggc   1020
gtgtcgtacg acgaggtggt ggagcagttg gagcaggagg gcgtggcgaa gttcgaggcg   1080
```

```
gcctggcagg agctgctcgc cgccgtgacg aagtccctcg acagcaaggg agttgacggg    1140
gaatga                                                              1146

<210> SEQ ID NO 15
<211> LENGTH: 1119
<212> TYPE: DNA
<213> ORGANISM: Streptomyces avermitilis

<400> SEQUENCE: 15
atgacagacg cactcaagcg cctctccaag gaaggcgtcg cgatctggct ggacgacctg     60
tcgcgcaagc ggatcacgtc cggcaacctc gccgaactga tcgaccagca gcacgtcgtg    120
ggcgtcacca ccaacccgtc gatcttccag aaggccatct ctcagggcga cggttacgac    180
cagcaggtct ccgacctcgc cgcccgccgg gtcaccgtcg aagaagccat ccgcatgatc    240
accacggcgg acgtccgcga cgccgccgac atcctgcgcc cggtcttcga cgccaccgac    300
ggccaggacg gccgggtctc gatcgaggtc gacccgcgcc tggcccacaa caccaaggcg    360
acggtcgccg aggccaagca gctggcctgg ctggtcgacc gccccaacac gctcatcaag    420
atcccggcca ccaaggcggg catcccggcg atcacggagg tcatcggcct cggcatcagc    480
gtcaacgtga cgctgatctt ctcgctcgag cgctaccgca tggtcatgga cgcctacctc    540
gccggcctgg agaaggccaa ggagcgcggc ctggacctgt cgaagatcca ctcggtggcg    600
tccttcttcg tgtcccgcgt ggacaccgag atcgacaagc ggatcgacgc cctcggcacg    660
ccggaggcca aggccgcgcg cggcaaggcg ggcctcgcca cgcccggct cgcctacgag    720 gcgtacgagg cggtcttctc caccgaccgc tggctcgccc tcgacaaggc gcaggccaac    780
aagcagcgcc cgctgtgggc ctccaccggc gtcaaggacc cggcgtacaa ggacaccatg    840
tacgtcgagg aactggtcgc gccgaacacc gtgaacacca tgccggaggc cactttggag    900
gccaccgcgg accacggcga gatcgggggc aacaccatcg ccggcacgta cgagcaggcc    960
cgcgccgacc tcgacgccgt cgagaagctc gggatcgcgt acgacgacgt ggtccagctc   1020
ctggaggaag agggcgtcga caagttcgag gcgtcctgga cgacctgct caagtcgacc   1080 gaggcggagc tccagcgcct cgccccctcg gagggctga                         1119

<210> SEQ ID NO 16
<211> LENGTH: 1137
<212> TYPE: DNA
<213> ORGANISM: Streptomyces avermitilis

<400> SEQUENCE: 16
atgatcactg tgagcaacac cgtcgaaaac ctcgagcgcc tctccgacga aggcgtctcc     60
atctggctgg acgatctgtc gcgcaagcgg atcacgtccg gcaacctcgc cgaactcatc    120
gcgcacaagc acgtggtggg cgtcaccacc aacccgtcca tcttccaggc cgccatcggc    180
tccggagagg gatacgagga gcagctggcc gatctggccg tgcgtggcgt cacggtcgac    240
gaggccgtgc gcatgatgac gaccgccgac gtgcgcgccg ccgccgacat cctgcggccc    300
gtgtacgacg cgaccggcgg ccgtgacggc cgggtctcca tcgaggtcga cccgcgcctc    360
gcccacgaca ccgaggcgac gatcgccgaa gccaagcagc tcgcctggct ggtggaccgc    420
cccaacgtga tgatcaagat tccggcgacc aaggccggtc tccccgcgat caccgaggtc    480
atcggcctcg gcatcagcgt caacgtcacg ctgatcttct cgctcgagcg ctaccgcgag    540
gtgatggacg cctacctcgc cggtctggag cgggcgcagg ccgcgggcat cgacctggcc    600
```

-continued

| | |
|---|---|
| ggcatccact ccgtcgcctc cttcttcgtc tcccgcgtcg acagcgagat cgacaagcgc | 660 |
| ctggcgaagg ccggcacgga cgacgcgcag gccctcaagg gcaaggcggc gctcgccaac | 720 |
| gcccggctcg cgtacgaggc gtacgaagag gtcttcgccg gggagcgctg gaccgcgctc | 780 |
| gccccggccg gcgcgcacaa gcagcgtccg ctgtgggcct cgacgggcgt gaaggacccg | 840 |
| gcgtacaagg acaccctgta cgtcgacgag ctggtcgctc ccggcacggt caacaccatg | 900 |
| ccggagggga ccttgaacgc caccgccgac acggcgaca tccacggcga cacggtgacc | 960 |
| ggcggctatg cccaggcccg cgccgacctg gccgccgtgg agcggctggg gatctcgtac | 1020 |
| gacgaggtcg tgaagcagct ggaggacgag gccgtcgcca agttcgaggt ggcgtggggc | 1080 |
| gacctgctgg aggccgtcgc gacctcgctg cgcggcaagg gagctgacgg cgaatga | 1137 |

<210> SEQ ID NO 17
<211> LENGTH: 1593
<212> TYPE: DNA
<213> ORGANISM: Streptomyces lividans

<400> SEQUENCE: 17

| | |
|---|---|
| atgtccgagc cggaagagca gcagcccgac atccacacga ccgcgggcaa gctcgcggat | 60 |
| ctcaggcgcc gtatcgagga agcgacgcac gccggttccg cacgcgccgt cgagaaacag | 120 |
| cacgccaagg gcaagctgac ggctcgtgag cgcatcgacc tcctcctcga cgagggctcc | 180 |
| ttcgtcgagc tggacgagtt cgcccggcac cgctccacca acttcggcct cgacgccaac | 240 |
| cgcccttacg gcgacggcgt cgtcaccggt tacggcaccg tcgacggccg ccccgtggcc | 300 |
| gtcttctccc aggacttcac cgtcttcggc ggcgcgctgg gcgaggtcta cggccagaag | 360 |
| atcgtcaagg tgatggactt cgcgctgaag accggctgcc cggtcgtcgg catcaacgac | 420 |
| tccggcggcg cccgcatcca ggagggcgtg cctcccctcg cgcctacgg cgagatcttc | 480 |
| cgccgcaaca cccacgcctc cggcgtgatc ccgcagatca gcctggtcgt cggcccgtgc | 540 |
| gcgggcggcg cggtctactc ccccgcgatc accgacttca cggtgatggt cgaccagacc | 600 |
| agccacatgt tcatcaccgg ccccgacgtc atcaagacgg tcaccggtga ggacgtcggc | 660 |
| ttcgaggagc tggcggcgc ccgcacccac aacaccgcct cgggcgtggc ccaccacatg | 720 |
| gcgggtgacg agaaggacgc cgtcgagtac gtcaagcagc tcctgtcgta cctgccgtcc | 780 |
| aacaacctgt ccgagccccc cgccttcccg gaggaggcgg acctcgcggt cacggacgag | 840 |
| gacgccgagc tggacgcgat cgtcccggac tcggcgaacc agccctacga catgcacagc | 900 |
| gtcatcgagc acgtcctgga cgacggcgag ttcttcgaga cccagcccct gttcgcaccg | 960 |
| aacatcctca ccggcttcgg ccgcgtggag ggccgcccgg tcggcatcgt cgccaaccag | 1020 |
| cccatgcagt tcgccgggtg cctggacatc accgcctccg agaaggcggc ccgcttcgtg | 1080 |
| cgcacctgcg acgccttcaa cgtccccgtg ctcaccttcg tggacgtccc cggcttcctg | 1140 |
| cccggcgtcg accaggagca cgacggcatc atccgccgcg cgccaagct gatcttcgcc | 1200 |
| tacgccgagg ccacggtgcc gctgatcacg gtcatcaccc gcaaggcctt cggcggcgcc | 1260 |
| tacgacgtca tgggctccaa gcacctgggc gccgacctca acctggcctg gccaccgcc | 1320 |
| cagatcgccc tcatgggcgc ccagggcgcg gtcaacatcc tgcaccgccg caccatcgcc | 1380 |
| gacgccggtg acgacgccga ggccacccgg gcccgcctga tccaggagta cgaggacgcc | 1440 |
| ctcctcaacc cctacacggc ggccgaacgc ggctacgtcg acgccgtgat catgccctcc | 1500 |
| gacactcgcc gccacatcgt ccgcggcctg cgccagctac gcaccaagcg cgagtccctg | 1560 |
| ccccccgaaga agcacggcaa catccccctg taa | 1593 |

<210> SEQ ID NO 18
<211> LENGTH: 1599
<212> TYPE: DNA
<213> ORGANISM: Streptomyces avermitilis

<400> SEQUENCE: 18

| | | | | | |
|---|---|---|---|---|---|
| atgtccgagc | cggaagagct | gcaccacccc | gatatccaca | ccaccgcggg | caaactcgcg | 60 |
| gatctgcagc | gccgcatcca | ggaggcgacg | cacgccggct | cggagcgcgc | cgtcgaaaag | 120 |
| cagcacgcca | agggcaagct | gacggcccgt | gagcggatcg | cgctgctgct | cgacgaggac | 180 |
| tccttcgtcg | agctggacga | gttcgcgcag | caccgctcca | cggacttcgg | catggagaac | 240 |
| aaccgcccgt | acggagacgg | tgtcgtcacc | gggtacggga | ccgtggacgg | ccgccccgtc | 300 |
| gccgtgttct | cgcaggactt | caccgtcttc | ggcggtgccc | tcggcgaggt | cttcgggcag | 360 |
| aagatcatga | aggcgatgga | cttcgccctg | aagacgggct | gtccggtcat | cggcatcaac | 420 |
| gactccggcg | cgcccgtat | ccaggagggc | gtctcggccc | tcggcatgta | cggcgagatc | 480 |
| ttccgccgca | cacccatgc | ctcgggcgtg | atcccgcaga | tcagcctggt | cgtcggcccg | 540 |
| tgcgcgggcg | cgcggtcta | ctcccccgcg | atcaccgact | tcacggtgat | ggtcgaccag | 600 |
| acctcgcaca | tgttcatcac | gggccccgac | gtcatcaaga | cggtgacggg | cgaggacgtc | 660 |
| ggcttcgagg | agctgggcgg | cgcccgcacg | cacaacgcgg | tgtcgggcgt | ggcccatcac | 720 |
| atggcggggg | aggagaagga | cgcgatcgag | tacgtcaagc | agctgctgtc | gtacctgccg | 780 |
| tccaacaacc | tcagcgagcc | gccggccttc | ccggaggagg | cggacctcgc | cctcaccgac | 840 |
| gaggaccgcg | agctggacac | cctcgtaccc | gacagtgcga | accagccgta | cgacatgcac | 900 |
| acggtgatcg | aacacatcct | ggacgacgcc | gagttcctgg | agacgcagcc | gctgttcgcg | 960 |
| ccgaacatcc | tcaccggctt | cggccgggtc | gagggccacc | cggtgggcat | cgtcgccaac | 1020 |
| cagccgatgc | agttcgcggg | ctgcctcgac | atcgacgcgt | ccgagaaggc | cgcccgcttc | 1080 |
| gtgcgcacct | gcgacgcgtt | caacgtcccg | gtgatcactt | tcgtggacgt | gccgggcttc | 1140 |
| ctgcccggtg | tcggccagga | gcacgacggc | atcatccgcc | gcggcgccaa | gctgatctac | 1200 |
| gcgtacgccg | aggcgaccgt | cccgctgatc | accgtcatca | cccgcaaggc | gttcggcggc | 1260 |
| gcgtacgacg | tcatgggctc | caagcacctg | ggcgccgacc | tcaacctcgc | ctggccgacc | 1320 |
| gcccagatcg | ccgtgatggg | cgcgcagggc | gcggtcaaca | tcctgcaccg | ccgcaccatc | 1380 |
| gccgccacac | ccgaggagga | gcgcgaggag | gtccgccggc | ggctcatcca | ggagtacgag | 1440 |
| gacacgctgc | tcaaccccta | cacggcggcc | gagcgcggct | acatcgacgg | cgtgatcatg | 1500 |
| ccgtccgaca | cccgcgccca | tgtcgtacgg | gggctgcgtc | agctccgtac | gaagcgggaa | 1560 |
| tccctgcctc | cgaagaagca | cggcaacatc | cccctctag | | | 1599 |

<210> SEQ ID NO 19
<211> LENGTH: 1719
<212> TYPE: DNA
<213> ORGANISM: Streptomyces lividans

<400> SEQUENCE: 19

| | | | | | |
|---|---|---|---|---|---|
| atgaccgtca | acgagcccgt | acctgacacc | ttcgaggaca | ccccgcggg | ggaccggcac | 60 |
| ccggactggt | tcaaacgagc | cgtcttctac | gaggtcctcg | tccgctcctt | ccaggacagc | 120 |
| aacggcgacg | gcatcggtga | tctcaagggc | ctgaccgcca | agctggacta | cctgcaatgg | 180 |
| ctcggcgtgg | actgcctgtg | gctcccgccc | ttcttcaagt | caccgctgcg | cgacggcggt | 240 |

```
tacgacgtct ccgactacac cgccgtgctg ccggagttcg cgacctggc cgacttcgtg    300 gagttcgtgg acgcggcgca ccagcgcggc atgcgcgtga tcatcgactt cgtcatgaac    360
cacaccagcg accagcaccc gtggttccag gagtcccgca agaacccgga cggcccctac    420
ggcgactact acgtctgggc cgacgacgac acccggtacg ccgacgcccg catcatcttc    480
gtcgacaccg aggcctccaa ctggacctac gacccggtcc gcggccagta ctactggcac    540
cggttcttct cccaccagcc ggacctcaac tacgagaacc cggccgtgca ggaggagatg    600
ctcgccgccc tgaagttctg gctggacctg ggcgtggacg gctaccgtct cgacgccgtg    660
ccctacctgt acgccgagga gggcaccaac tgcgagaacc tgcccgcctc ccacgcgttc    720
ctcaagcggg tgcgccgcga gatcgacgca cagtacccgg acaccgtact gctggccgag    780
gccaaccagt ggccggagga cgtggtcgac tacttcggcg actactccac gggcggcgac    840
gagtgccaca tggccttcca cttccccgtc atgccccgca tcttcatggc cgtgcgccgc    900
gagtcccgct acccggtctc cgaaatcctc gccaagaccc ccgcgatccc gtccggctgc    960
cagtggggca tcttcctgcg caaccacgac gagctgaccc tggagatggt caccgacgag   1020
gaacgcgact acatgtacgc ggagtacgcc aaggacccgc gcatgcgcgc caacatcggt   1080
atccgccggc ggctggccac cctgctggac aacgaccgcg accagatcga gctgttcacc   1140
gccctgctgc tcgccctccc gggatccccg atcctctact acggcgacga gatcggcatg   1200
ggcgacaaca tctggctcgg cgaccgcgac gccgtgcgca cccccatgca gtggacgccc   1260
gaccgcaacg ccggcttctc gacctgtgac ccgggccgcc tctacctgcc cgcgatcatg   1320
gacccggtct acggctacca ggtgacgaac gtcgaggcgt ccatggcctc gccctcctcc   1380
ctgctgcact ggacccggcg catgatcgag atccgcaagc agaacccggc cttcggcctc   1440
ggcacctaca ccgaactgcc ctcctccaac ccggcggtgc tcgccttcct gcgggagtac   1500
gaggacgacc tggtgctgtg tgtgaacaac ttcgcacggt tcgcccagcc caccgagctg   1560
gatctgcgcg agttcgccgg acgccatccg gtcgagctgt tcggcggggt ccgcttcccc   1620
gccatcggcg aactgccgta cctgctgacc ctcggggggcc acggcttcta ctggttccgg   1680
ctcacccgag tcgcatcccg catcggccgc cgcgcttga                          1719
```

<210> SEQ ID NO 20
<211> LENGTH: 1752
<212> TYPE: DNA
<213> ORGANISM: Streptomyces avermitilis

<400> SEQUENCE: 20

```
atgatcgtca acgagcccgt cccggacacc ttcgaggaca cgcccgccaa ggaccgcgat     60
ccggagtggt tcaaacgcgc cgtcttctac gaggtcctgg tccgctcctt ccaggacagc    120
aacggcgacg gtgtcggcga cctgaagggc ctgaccgcca agctggacta tctgcagtgg    180
ctgggcgtgg actgcctgtg gctgccgccg ttcttcaagt cccccctgcg cgacggcggc    240
tacgacgtct ccgactacac cgcggtgctg cccgagttcg gtgacctggc cgacttcgtc    300
gagttcgtgg acgcggccca ccagcgcggc atgcgcgtga tcatcgactt cgtgatgaac    360
cacaccagtg acctgcatcc gtggttccag gagtcccgca gcaacccccga cggcccctac    420 ggcgactact acgtgtgggc cgacgacgac aagcagtacc aggacgcccg gatcatcttc    480
gtcgacaccg aggcctccaa ctggacgtac gacccggtcc gcaagcagta ctactggcac    540
cgcttcttct cccaccagcc cgacctcaac tacgagagtg ccgccgtcca ggaggagatc    600
ctggcggcgc tgcggttctg gctcgatctg ggcatcgacg gcttcaggct ggacgccgtc    660
```

```
ccctacctgt acaacgaaga ggggacgaac tgcgagaacc tgccggcgac gcacgagttc      720
ctgaagcggg tgcgcaagga gatcgacacg cactatccgg acacggtgct gctcgcggag      780
gcgaaccagt ggccggagga cgtggtcgac tacttcggcg acttcccctc gggcggcgac      840
gagtgccaca tggcgttcca tttcccggtc atgccgcgga tcttcatggc ggtgcggcgt      900
gagtcgcggt atccggtgtc ggagatcctg gcgaagacgc cggcgatccc gtcgagctgc      960
cagtggggca tcttcctgcg caaccacgac gagctgaccc tggagatggt caccgacgag     1020
gaacgcgact acatgtgggc ggagtacgcc aaggatccgc ggatgcgggc caacatcggc     1080
atccgccggc gtctggcgcc gctgctggac aacgaccgca accagatcga gctgttcacc     1140
gcgctgctgc tgtcgctgcc cggctcgccg atcctctact acggcgacga gatcgggatg     1200
ggggacaaca tctggctcgg tgaccgggac gcggtgcgca cgccgatgca gtggacgccg     1260
gaccgcaacg cgggtttctc gtcctgcgac ccggggcgtc tgtatctgcc cacgatcatg     1320
gatccggtct acgggtacca ggtcacgaac gtggaggcgt cgatgtcgtc gccgtcctcg     1380
ctgctgcact ggacccggcg gatgatcgag atccgtaagc agaacccggc gttcggcctc     1440
ggctcgtaca ccgaactcca gtcctcgaac ccggccgtcc tcgcgttcct gcgggaggcc     1500
ccctcgaccg gggggaacgg ggacgacctg gtgctgtgcg tgcacaactt ctcccggttc     1560
gcgcagccca cggagctgga tctgcgggcg ttcagcggcc gtcatccggt cgagctgatc     1620
ggcggtgtcc gcttcccggc catcggggaa ctcccgtatc tgctgaccct gcaggccac      1680 ggcttctact ggttccggct ccgcaaggac gtcacccagg tcaccaaggt gagcttgttc     1740
gtgagctctt ga                                                         1752

<210> SEQ ID NO 21
<211> LENGTH: 1701
<212> TYPE: DNA
<213> ORGANISM: Streptomyces lividans

<400> SEQUENCE: 21
atgaccgtca acgagcccgt acctgacacc ttcgaggaca cccccgcggg ggaccggcac       60
ccggactggt tcaaacgagc cgtcttctac gaggtcctcg tccgctcctt ccaggacagc      120
aacggcgacg gcatcggtga tctcaagggc ctgaccgcca agctggacta cctgcaatgg      180
ctcggcgtgg actgcctgtg ctcccgcgcc ttcttcaagt caccgctgcg cgacggcggt      240
tacgacgtct ccgactacac cgccgtgctg ccggagttcg gcgacctggc cgacttcgtg      300
gagttcgtgg acgcggcgca ccagcgcggc atgcgcgtga tcatcgactt cgtcatgaac      360
cacaccagcg accagcaccc gtggttccag gagtcccgca ggaacccgga cggcccctac      420
ggcgactact acgtctgggc cgacgacgac aagcagttcc aggacgcgcg gatcatcttc      480
gtcgacaccg aggcgtccaa ctggacctac gacccggtgc gcaagcagta ctactggcac      540
cggttcttct cccaccagcc ggacctcaac tacgagaacc cggtcgtgca ggaggagatg      600
atctccgcgc tgaagttctg gctggacctg gcatcgacg ggttccggct ggacgcggtg      660
ccgtacctct accaggagga gggcaccaac tgcgagaacc tcccgcgcac gcacgacttc      720
ctgaagcggg tgcgcaagga gatcgacgcg cagtacccgg acacggtggt gctggccgag      780
gccaaccagt ggccggagga cgtggtcgac tacttcggcg actacgcggc gggcggcgac      840
gagtgccaca tggccttcca cttccccgtc atgccccgca tcttcatggc ggtcagaagg      900
gagtcccgct acccggtctc cgaaatcctg gccaagaccc cggccatccc gtccggctgc      960
```

```
cagtggggca tcttcctgcg caaccacgac gagctgaccc tggagatggt caccgacgag    1020
gaacgcgact acatgtacgc ggagtacgcc aaggacccgc gcatgcgcgc caacatcggc    1080
atccggcgca ggctcgcccc gctcctcgac aacgaccgca accagatcga gctgttcacc    1140
gccctgctgc tgtccctgcc cggctcgccg atcctctact acggcgacga gatcggcatg    1200
ggcgacaaca tctggctcgg cgaccgcgac gccgtgcgca cccccatgca gtggacgccc    1260
gaccgcaacg cgggcttctc gtcgtccgac ccgggccgcc tgttcctgcc cacgatcatg    1320
gacccggtcc acggttacca ggtgacgaac gtcgaggcgt ccatggcctc gccctcctcc    1380
ctgctgcact ggacccggcg catgatcgag atccgcaagc agaacgtggc cttcggcctg    1440
ggcacctaca ccgagctgcc gtcgtccaac cctgccgtcc tggccttcct gcgcgaacac    1500
gaggacgacc tggtgctgtg cgtccacaac ttctcccggt tcgcgcagcc gacggagctg    1560
gacctcagcg ccttcgacgg acgccatccg gtcgagctgt tcggcggggt ccgcttcccg    1620
gcggtcggtg acctgccgta cctgctgacc ctgggcggtc acggcttcta ctggttccgc    1680
ctgcgcaagg acgccgcctg a                                              1701
```

<210> SEQ ID NO 22
<211> LENGTH: 1719
<212> TYPE: DNA
<213> ORGANISM: Streptomyces avermitilis

<400> SEQUENCE: 22

```
atgatcgtca acgagcccgt cccggacacc ttcgaggaca cgcccgccaa ggaccgcgat      60
ccggagtggt tcaaacgcgc cgtcttctac gaggtcctgg tccgctcctt ccaggacagc     120
aacggcgacg gtgtcggcga cctgaagggc ctgaccgcca agctggacta tctgcagtgg     180
ctgggcgtgg actgcctgtg gctgccgccg ttcttcaagt cccccctgcg cgacggcggc     240
tacgacgtct ccgactacac cgcggtgctg ccgagttcg gtgacctggc cgacttcgtc      300
gagttcgtgg acgcggccca ccagcgcggc atgcgcgtga tcatcgactt cgtgatgaac     360
cacaccagcg acctgcaccc gtggttccag gagtcccgca gcaaccccga cggcccctac     420
ggcgactact acgtgtgggc cgacgacgac aagcagtacc aggacgcccg gatcatcttc     480
gtcgacaccg aggcctccaa ctggaccttc gacccggtcc gcaagcagta ctactggcac     540
cgcttcttct cccaccagcc cgacctcaac tacgagaacc cggcggtgca ggaggagatc     600
gtctccgccc tgcggttctg gctcgacctc ggcatcgacg gcttccgcct cgacgcggtg     660
ccgtacctgt accagcagga aggcaccaac tgcgagaacc tgccggcgac gcacgagttc     720
ctgaagcggg tgcgcaagga gatcgacacg cactatccgg acacggtgct gctcgcggag     780
gcgaaccagt ggccggagga cgtggtcgac tacttcggcg acttcccctc gggcggcgac     840
gagtgccaca tggcgttcca tttcccggtc atgccgcgga tcttcatggc ggtgcggcgt     900
gagtcgcggt atccggtgtc ggagatcctg gcgaagacgc cggcgatccc gtcgagctgc     960
cagtggggca tcttcctgcg caaccacgac gagctgaccc tggagatggt caccgacgag    1020
gaacgcgact acatgtgggc ggagtacgcc aaggatccgc ggatgcgggc caacatcggc    1080
atccggcggc gtctggcgcc gctgctggac aacgaccgca accagatcga gctgttcacc    1140
gcgctgctgc tgtcgctgcc cggctcgccg atcctctact acggcgacga gatcggcatg    1200
ggggacaaca tctggctcgg tgaccgggac gcggtgcgca ctccgatgca gtggacgccg    1260
gaccgcaacg cgggtttctc gtcctgcgac ccggggcgtc tgtatctgcc cacgatcatg    1320
gatccggtct acgggtacca ggtcacgaac gtggaggcgt cgatgtcgtc gccgtcctcg    1380
```

```
ctgctgcact ggacccggcg gatgatcgag atccgtaagc agaacccggc gttcggcctc    1440
ggctcgtaca ccgaactcca gtcctcgaac ccggccgtcc tcgcgttcct gcgggaggcc    1500
ccctcgaccg gggggaacgg ggacgacctg gtgctgtgcg tgcacaactt ctcccggttc    1560
gcgcagccca cggagctgga tctgcgggcg ttcagcggcc gtcatccggt cgagctgatc    1620
ggcggtgtcc gcttcccggc catcggggaa ctcccgtatc tgctgaccct ggcaggccac    1680
ggcttctact ggttccggct ccgcaaggac gccgtctag                           1719
```

<210> SEQ ID NO 23  
<211> LENGTH: 2115  
<212> TYPE: DNA  
<213> ORGANISM: Streptomyces lividans

<400> SEQUENCE: 23

```
gtgttcatgc aggtctggcc tggagaggcg tatccactgg gtgccacgta cgacggcgcc      60
ggcaccaact tcgcggtctt cacggaggcc gccgaccgag tagagctgtg tctgctgcac    120
gacgacggtt cggagacggc ggtcgagctg cgggagagcg atgccttcgt gcggcacgcg    180
tacgtgccgg gcgtgatgcc ggggcagcgg tacggctacc gcgtgcacgg cccgtacgcc    240
ccggagcgcg gactgcgctg caacagcgcc aagctgctcc tcgatccgta cgcgcgtgcg    300
atcagcgggg aggtccagtg gggcgaggag gtgtacggct accacttcgg cgcacccgaa    360
cggcgcaacg acctcgactc ggccccgcac acgatgacgt cggtcgtggt caacccgtac    420
ttcgactggg gcgacgaccg gcgccccccgt acggagtacc accacacggt gatctacgag    480
gcccacgtga agggcctgac catgcgccac ccgggcctgc ccgaggagct gcggggcacc    540
tacgcggccc tcgcgcaccc ggcgctcatc gagcacctca cggggctcgg ggtgaccgcg    600
ctggagctga tgccggtcca tcagttcgtc aacgaccacc ggctggtgga catgggcctc    660
aacaactact ggggctacaa cacggtcggg ttcttcgccc cgcacaacgc ctacgcctcc    720
tggggcgacc gcggccagca ggtgctggag ttcaagtccg cggtcaaggc gctgcacgag    780
gcggggatcg aggtgatcct cgacgtggtc tacaaccaca ccgcggaggg caaccacctg    840
ggcccgacgc tgtccttcaa ggggctggac aaccctcgt actaccggct ggccgacgac    900
ccccgctact acatggacac cacggggacc gggaactcgc tgctcatgcg gtccccgcac    960
gtactccaga tgatcatgga ctcactgcgg tactgggtca ccgagatgca cgtggacggg   1020
ttccgtttcg acctcgcggc cacgctggcc cggcagttcc acgaggtgga ccggctgtcg   1080
tcgttcttcg acctggtgca gcaggacccc gtggtctcgc aggtgaagct gatcgccgag   1140
ccgtgggacg tgggcgaggg cggctaccag gtgggcaact cccgccgct gtggaccgag   1200 tggaacggca agtaccggga cacggtgcgg gacctgtggc gcggcgagcc gcgcacgctg   1260
gcggagttcg cgtcccggct gaccggttcc tccgacctct accaggacga cgggcgccgc   1320
ccgctggcct cgatcaactt cgtgacctgc acgacggct tcaccctgca cgacatggtg   1380
gcctacaacg acaagcacaa ccacgccaac ggcgaggaca accgggacgg cgagagccac   1440
aaccgttcct ggaactgcgg tgtcgagggc gacaccgacg atccggcggt gctggagctg   1500
cgggcgcggc agatgcgcaa cttcatcgcc acgctgctgc tctcccaggg cgtcccgatg   1560
ctcagccacg cgacgagtt cgcccgcacc cagcggggca acaacaacgc ctactgccag   1620
gacaacgagc tggcgtgggt ggcgtggccc gaggacggcc acgacctcct ggagttcacc   1680
cgcgcgatgg tctggctgcg caaggaccac ccggtcctgc gcaggcgccg cttcttccac   1740
```

```
gggcgcccgg tgcagggcac ccacgacgag ctgtcggaca tcgcctggtt cacgccggag    1800
ggcgcggaga tggcccagcg ggactggaac tcggcacggg cctccgcgct cacggtcttc    1860
ctgaacggca acgcgatctc cgagcccggc acccgcgggg aacgcatcgc cgacgattcg    1920
ttcctgctga tgttcaacgc cgcgccgagg ccgctggact tcgtggtgcc ggtcgatcac    1980
ggccggcagt gggaggtggt cgtcgacacc gctctgacgg ccggggtgcc cacgggcacg    2040
ggcccgaagg tgcaggccgg ggaccggctg accctcctgg accggagcct gacggtgttg    2100
cagcggccgg tgtag                                                     2115

<210> SEQ ID NO 24
<211> LENGTH: 2109
<212> TYPE: DNA
<213> ORGANISM: Streptomyces avermitilis

<400> SEQUENCE: 24
atgcaggtct ggcctggaga ggcatatcca ctcggcgcca cgtacgacgg cgccggtacc     60
aatttcgcgc tcttctcgga ggccgcccat cggatcgagc tgtgtctgct gcacgacgac    120
ggctcggaga cggcggtgga actgagggag accgacgcgt tcgtgcggca cgcgtatctg    180
cccggcgtca tgccggggca gcggtacggc ttccgcgtgc acggcccgtt cgcgccgggg    240
cgcggggtgc gctgcaattc cgccaagctg ctgctcgatc cgtacgcgaa ggcgatcagc    300
ggcgagatca agtggggcga ggaggtgtac ggctaccact cggcgcccc cgacaagcgc    360 aacgacctgg actcggcgcc gcacacgatg acctcggtcg tgatcaaccc gtacttcgac    420
tggggcaacg accggcggcc gcgcaccgag taccaccaca cagtgctcta cgaggcccat    480
gtgaagggcc tgacgatgcg gcatcccgcg ctgcccgagg aactgcgcgg cacgtatgcg    540
gcgctcgccc accccgccat catcgaacac ctgactgaac tgggcgtcac cgcgctcgaa    600
ctgatgccgg tgcaccagtt cgtgaacgac caccgtctgg tggacatggg cctgaacaac    660
tactggggct acaacacgat cggtttcttc gccccgcaca acgcgtacgc ctcctggggc    720
gaccgcggcc agcaggtgct ggagttcaag tcggcagtga aggcgctgca cgaggccggg    780
atcgaggtca tcctggacgt ggtctacaac cacacggccg agggcaacca catgggcccg    840
acgctctcct tcaagggcat cgacaacgcg tcgtactacc ggctcaccga cgatccccgc    900
tactacatgg acaccacggg gaccgggaac tccctcctca tgcgctcccc gcacgtcctc    960
caactgatca tggactcgct cgctactggg gtcagcgaca tgcatgtcga cggcttccgc    1020
ttcgacctcg cggccaccct ggcccggcag ttccacgagg tggaccggct gtcgtcgttc    1080
ttcgacctgg tccagcagga cccggtggtc tccaggtga agctgatcgc cgagccgtgg    1140
gacgtcggcg agggcggcta ccaggtgggc aacttcccgc cgctgtggac cgagtggaac    1200
ggcaagtacc gcgacacggt gcgggacatg tggcggggcg agccgcgtac gctcgcggag    1260
ttcgcctccc gcctgacggg ctcgtcggac ctctaccagg acgacggccg ccgtcccctc    1320
gcctccatca acttcgtcac ctgccacgac ggtttcaccc tgcacgacct cgtcgcgtac    1380
aacgacaagc acaaccaggc caacggcgag acaaccgggc acggggagag ccacaaccgg    1440
tcctggaact gcggggccga gggcgacacc gacgatccgg cggtgctggc gttgcgggcg    1500
cgccagatgc gcaacttcat cgccacgctg atgctctcgc agggcgtgcc gatgctcagc    1560
cacggggatg agttcgcgcg cacccagggc ggcaacaaca acgcgtactg ccaggacggc    1620
gagctgtcgt gggtggcgtg gcccgaggac ggcagcgagc tgctggagtt cacgcgcgcg    1680
atggtgtggc tgcggcgcga ccatccggtc ttccggcgcc gccgcttctt ccacgggcgg    1740
```

```
ccggtggagg gcacgcacga cgagctgtcg gacatcgtct ggttcacgcc gacgggtgag    1800
gagatgatcc agcgcgactg ggattcggcg caggcacggg cgctgacggt gttcctcaac    1860
ggcaccgcga tctccgagcc cggcccacgc ggagagcgga tctcggacga ctccttcctg    1920
ttgatgttca acgcctcccc gaagtcgctg gagttcgtgg tgccggtcga ccacggccgc    1980
cagtggcagg tcgtcgtcga cacggcacgc acggacggga tcccgccggg cacggtcgcg    2040
aaggtcaagg ccggggaccg gctgacgctg gtggaccgga gcctcacggt gttgcagcgg    2100
ccggcctga                                                            2109
```

<210> SEQ ID NO 25  
<211> LENGTH: 30  
<212> TYPE: DNA  
<213> ORGANISM: Artificial Sequence  
<220> FEATURE:  
<223> OTHER INFORMATION: Primer

<400> SEQUENCE: 25

```
aagatcccgg tcttcgaggc gggcaagggc                                        30
```

<210> SEQ ID NO 26  
<211> LENGTH: 30  
<212> TYPE: DNA  
<213> ORGANISM: Artificial Sequence  
<220> FEATURE:  
<223> OTHER INFORMATION: Primer

<400> SEQUENCE: 26

```
gcggcgtagg tgtcggtctt cgacttgggg                                        30
```

<210> SEQ ID NO 27  
<211> LENGTH: 28  
<212> TYPE: DNA  
<213> ORGANISM: Artificial Sequence  
<220> FEATURE:  
<223> OTHER INFORMATION: Primer

<400> SEQUENCE: 27

```
caaaggccgc aacaacaccc tctccgcc                                          28
```

<210> SEQ ID NO 28  
<211> LENGTH: 26  
<212> TYPE: DNA  
<213> ORGANISM: Artificial Sequence  
<220> FEATURE:  
<223> OTHER INFORMATION: Primer

<400> SEQUENCE: 28

```
tagcccgcgc agaacgcctc ccggca                                            26
```

<210> SEQ ID NO 29  
<211> LENGTH: 26  
<212> TYPE: DNA  
<213> ORGANISM: Artificial Sequence  
<220> FEATURE:  
<223> OTHER INFORMATION: Primer

<400> SEQUENCE: 29

```
cccaggatga gcccctcgag gcgcag                                            26
```

<210> SEQ ID NO 30  
<211> LENGTH: 29  
<212> TYPE: DNA

```
<213> ORGANISM: Artificial Sequence
<220> FEATURE:
<223> OTHER INFORMATION: Primer

<400> SEQUENCE: 30
ctgatcgtgc tgctgctgat gacgtacga                                      29

<210> SEQ ID NO 31
<211> LENGTH: 30
<212> TYPE: DNA
<213> ORGANISM: Artificial Sequence
<220> FEATURE:
<223> OTHER INFORMATION: Primer

<400> SEQUENCE: 31
tccgccgacc tggccggctc gaacaacacc                                     30

<210> SEQ ID NO 32
<211> LENGTH: 30
<212> TYPE: DNA
<213> ORGANISM: Artificial Sequence
<220> FEATURE:
<223> OTHER INFORMATION: Primer

<400> SEQUENCE: 32
gccagccggc cgcgtactgt ccgcggacgg                                     30
```

METHOD FOR PRODUCING SEDOHEPTULOSE

RELATED APPLICATION

This application claims the benefit of priority of application number 2018-087503 filed with the Japan Patent Office on Apr. 27, 2018. The contents of the priority application is incorporated herein by reference.

TECHNICAL FIELD

The present invention relates to a method for producing sedoheptulose by a bacterium, a method for improving the productivity of sedoheptulose by the bacterium, and the bacterium for the methods.

BACKGROUND

Sedoheptulose, which is a saccharide falling within the categories of ketoses and heptuloses, is one of a small number of heptuloses occurring in nature. Sedoheptulose is a constituent sugar of D-sedoheptulose-7-phosphate in the pentose phosphate pathway, which is a metabolic system of a living organism. A method using a bacterium has been reported as a method for producing sedoheptulose. So far, it has been reported that *Streptomyces naraensis* (Patent literatures 1-2 and non-Patent literature 1), *Streptomyces albus* (non-Patent literature 1 and Patent literature 3), *Streptomyces californicus* (non-Patent literature 1 and Patent literature 3), *Streptomyces sindensis* (non-Patent literature 1), *Streptomyces olivaceus* (non-Patent literature 1), *Streptomyces vividochromogenus* (non-Patent literature 1), and *Flavobacterium* sp. TSC-A, *Achromobacter* sp. TSC-B (Patent literature 4) can produce sedoheptulose as the bacterium. In the above-mentioned literatures, bacteria that produce sedoheptulose in the natural world have been reported, but no method for improving the productivity of sedoheptulose in these bacteria is known. It is known that an addition of ribose to *Bacillus subtilis* mutated in transketolase improves the productivity of sedoheptulose (maximum production is 25 g/L, production is 5 g/L when ribose is absent) (Patent literature 5). As a method for producing sedoheptulose other than using a bacterium, methods using transketolase (Non-patent literatures 2 and 3) and a method by chemical synthesis (Patent literature 6) have been reported.

PRIOR ART DOCUMENTS

Patent Literatures

[Patent literature 1] JP S39-14500 B
[Patent literature 2] JP S41-4400 B
[Patent literature 3] JP S41-5915 B
[Patent literature 4] JP S41-21760 B
[Patent literature 5] JP S62-126990 A
[Patent literature 6] SK284318

Non-Patent Literatures

[Non-patent literature 1] Accumulation of sedoheptulose by Streptomycetes. J. Biochem. 1963; 54(1):107-8
[Non-patent literature 2] An efficient synthesis of sedoheptulose catalyzed by Spinach Transketolase, Tetrahedron Asymmetry. 1993; 4: 1169-1172
[Non-patent literature 3] Heptulose synthesis from nonphosphorylated aldoses and ketoses by Spinach transketolase, J. Biol chem. 1971 25; 246(10):3126-31.
[Non-patent literature 4] Crystal structures and mutational analyses of Acyl-CoA carboxylase β subunit of *Streptomyces coelicolor*. Biochemistry 2010; 49(34):7367-7376
[Non-patent literature 5] Subinhibitory concentrations of antibiotics induce phenazine production in a marine *Streptomyces* sp. J Nat Prod. 2008 May; 71(5):824-827

SUMMARY OF INVENTION

Problems to be Solved by the Invention

A problem to be solved by the present invention is to provide a method for producing sedoheptulose by a bacterium, a method for improving the productivity of sedoheptulose by the bacterium, and the bacterium for the methods.

Means for Solving the Problem

The present invention provides:
(1) a method for producing sedoheptulose, including culturing a bacterium in which a function of transaldolase is deleted or attenuated;
(2) the method according to (1), where the bacterium is a bacterium in which a function of propionyl CoA carboxylase or a function of trehalose synthase is further deleted or attenuated;
(3) the method according to (1) or (2), where the bacterium is actinomycete, *Bacillus subtilis*, a bacterium belonging to *Flavobacterium*, or a bacterium belonging to *Achromobacter*;
(4) the method according to (3), where the bacterium is actinomycete;
(5) the method according to (4), where the actinomycete is a bacterium belonging to *Streptomyces*;
(6) the method according to (5), where the bacterium belonging to *Streptomyces* is *Streptomyces lividans* or *Streptomyces avermitilis*;
(7) a bacterium in which a function of transaldolase and a function of propionyl CoA carboxylase or a function of trehalose synthase are deleted or attenuated;
(8) the bacterium according to (7), where the bacterium is actinomycete, *Bacillus subtilis*, a bacterium belonging to *Flavobacterium*, or a bacterium belonging to *Achromobacter*;
(9) the bacterium according to (8), where the bacterium is actinomycete;
(10) the bacterium according to (9), where the bacterium is a bacterium belonging to *Streptomyces*; or
(11) the bacterium according to (10), where the bacterium is *Streptomyces lividans* or *Streptomyces avermitilis*.

Effect of the Invention

The present invention provides a method for producing sedoheptulose by a bacterium, a method for improving the productivity of sedoheptulose by the bacterium, and the bacterium for the methods.

MODES FOR CARRYING OUT THE INVENTION

Figure 1:
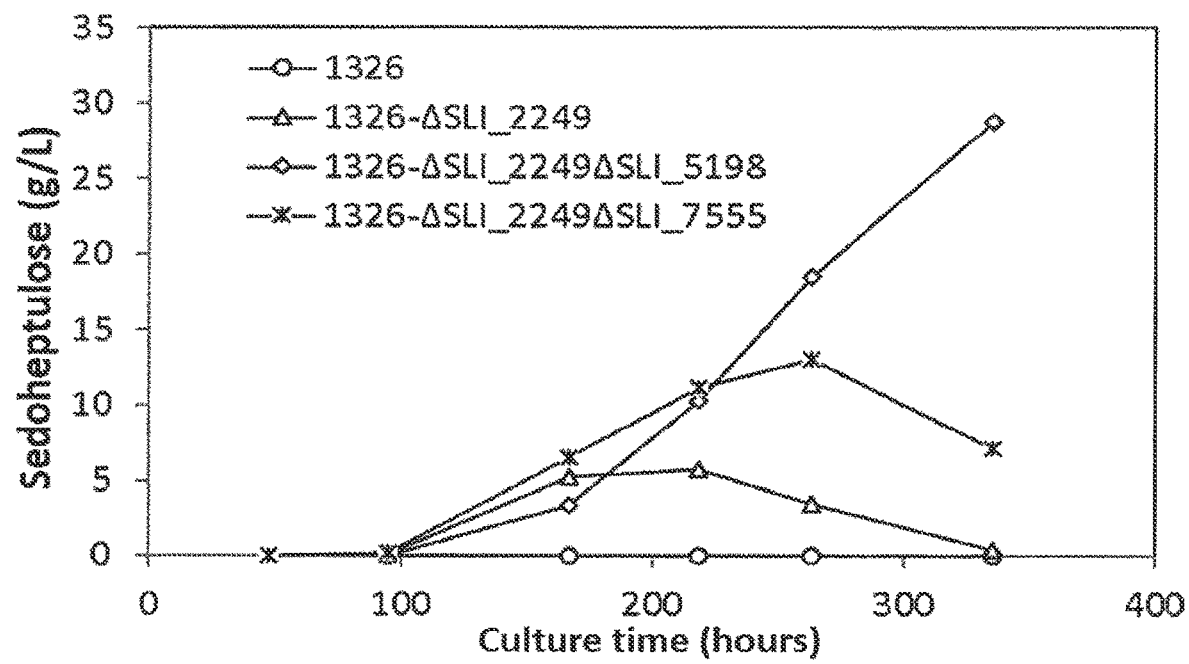
FIG. 1 shows the results of the production of sedoheptulose using *Streptomyces lividans* strain 1326.

In one aspect, the present invention relates to a method for producing sedoheptulose, including culturing a bacterium in which the function of transaldolase is deleted or attenuated.

In another aspect, the present invention relates to a bacterium in which a function of transaldolase is deleted or attenuated.

In yet another aspect, the present invention relates to a method for improving a productivity of sedoheptulose, including culturing a bacterium in which a function of transaldolase is deleted or attenuated.

In the present disclosure, sedoheptulose refers to sedoheptulose represented by the molecular formula $C_7H_{14}O_7$. For sedoheptulose, D-type and L-type are not particularly limited, but sedoheptulose is preferably D-sedoheptulose.

In the present disclosure, transaldolase enables to catalyze a reaction of converting sedoheptulose-7-phosphate and glyceraldehyde-3-phosphate to erythrose-4-phosphate and fructose-6-phosphate, and the reaction is reversible. Transaldolase is, for example, SLI_2249 (SEQ ID NO: 1) and SLI 7007 (SEQ ID NO: 2) for *Streptomyces lividans* and sav6314 (SEQ ID NO: 3) and sav1767 (SEQ ID NO: 4) for *Streptomyces avermitilis*.

[Sequence 1]
(SEQ ID NO: 1)
MTDALKRLSDEGVAIWLDDLSRKRITSGNLAELIDQQHVVGVTTNPSIF

QKAISQGDGYDQQLADLAVRGVTVEEAIRMITTADVRDAADILRPVYDN

TGGKDGRVSIEVDPRLAHNTHATVAEAKQLAWLVDRPNTFIKIPATEAG

LPAIAETIGLGISVNVTLIFSLERYRKVMDAFLTGLEKAKERGLDLSQI

HSVASFFVSRVDTEIDKRIDALGTDEAKAQRGKAAVANARLAYQAYEEV

FGTDRWAALEKAGANKQRPLWASTGVKDKAYSDTMYVTDLVAPNTVNTM

PEATLLATEDHGEITGDAVAGSYERARADLDAIEKLGISYDEVVQLLEK

EGVDKFEDAWNDLLKSTEAELKRLAPSKG

[Sequence 2]
(SEQ ID NO: 2)
MITVTEATATAGALQRLADQGVSVWLDDLSRRRIESGNLAELIRTKNVV

GVTTNPSIFQAAIGSGEGYEEQLADLATRGVTVDEAVRMMTTADVRAAA

DVLRGVYDASGGRDGRVSIEVDPRLAHDTAATVAEARQLSWLVDRPNVM

IKIPATKAGLPAITEVIGAGISVNVTLIFSLERYREVMDAYLAGLEKAQ

AAGIDLAGIHSVASFFVSRVDSEIDKRLSLLGTEEALGLRGRAALANAR

LAYEAYENVFAGDRFTALAGARANPQRPLWASTGVKDPAFRDTLYVEEL

VAPGTVNTMPEATLDAAADHGDVRGDTVTGGYAQARADLAAVERLGVSY

DEVVEQLEQEGVAKFEAAWQELLAAVTKSLDSKGVDGE

[Sequence 3]
(SEQ ID NO: 3)
MTDALKRLSKEGVAIWLDDLSRKRITSGNLAELIDQGHVVGVTTNPSIF

QKAISQGDGYDGQVSDLAARRVTVEEAIRMITTADVRDAADILRPVFDA

TDGQDGRVSIEVDPRLAHNTKATVAEAKGLAWLVDRPNTLIKIPATKAG

IPAITEVIGLGISVNVTLIFSLERYRMVMDAYLAGLEKAKERGLDLSKI

HSVASFFVSRVDTEIDKRIDALGTPEAKAARGKAGLANARLAYEAYEAV

FSTDRWLALDKAQANKGRPLWASTGVKDPAYKDTMYVEELVAPNTVNTM

PEATLEATADHGEIRGNTIAGTYEGARADLDAVEKLGIAYDDVVQLLEE

EGVDKFEASWNDLLKSTEAELQRLAPSEG

[Sequence 4]
(SEQ ID NO: 4)
MITVSNTVENLERLSDEGVSIWLDDLSRKRITSGNLAELIAHKHVVGVT

TNPSIFQAAIGSGEGYEEQLADLAVRGVTVDEAVRMMTTADVRAAADIL

RPVYDATGGRDGRVSIEVDPRLAHDTEATIAEAKQLAWLVDRPNVMIKI

PATKAGLPAITEVIGLGISVNVTLIFSLERYREVMDAYLAGLERAQAAG

IDLAGIHSVASFFVSRVDSEIDKRLAKAGTDDAQALKGKAALANARLAY

EAYEEVFAGERWTALAPAGAHKQRPLWASTGVKDPAYKDTLYVDELVAP

GTVNTMPEGTLNATADHGDIHGDTVTGGYAQARADLAAVERLGISYDEV

VKQLEDEAVAKFEVAWGDLLEAVATSLRGKGADGE

In the present disclosure, propionyl CoA carboxylase may catalyze a carboxylation reaction of propionyl CoA to produce methylmalonyl CoA. Propionyl CoA carboxylase is, for example, SLI_5198 (SEQ ID NO: 5) and sav_3331 (SEQ ID NO: 6). Propionyl CoA carboxylase is also known as an enzyme involved in the synthesis of secondary metabolites (Non-patent literature 4).

[Sequence 5]
(SEQ ID NO: 5)
MSEPEEQQPDIHTTAGKLADLRRRIEEATHAGSARAVEKGHAKGKLTAR

ERIDLLLDEGSFVELDEFARHRSTNFGLDANRPYGDGVVTGYGTVDGRP

VAVFSQDFTVFGGALGEVYGQKIVKVMDFALKTGCPVVGINDSGGARIQ

EGVASLGAYGEIFRRNTHASGVIPGISLVVGPCAGGAVYSPAITDFTVM

VDQTSHMFITGPDVIKTVTGEDVGFEELGGARTHNTASGVAHHMAGDEK

DAVEYVKQLLSYLPSNNLSEPPAFPEEADLAVTDEDAELDAIVPDSANQ

PYDMHSVIEHVLDDGEFFETGPLFAPNILTGFGRVEGRPVGIVANQPMQ

FAGCLDITASEKAARFVRTCDAFNVPVLTFVDVPGFLPGVDQEHDGIIR

RGAKLIFAYAEATVPLITVITRKAFGGAYDVMGSKHLGADLNLAWPTAQ

IAVMGAQGAVNILHRRTIADAGDDAEATRARLIQEYEDALLNPYTAAER

GYVDAVIMPSDTRRHIVRGLRQLRTKRESLPPKKHGNIPL

[Sequence 6]
(SEQ ID NO: 6)
MSEPEELHHPDIHTTAGKLADLGRRIQEATHAGSERAVEKGHAKGKLTA

RERIALLLDEDSFVELDEFAQHRSTDFGMENNRPYGDGVVTGYGTVDGR

PVAVFSQDFTVFGGALGEVFGQKIMKAMDFALKTGCPVIGINDSGGARI

QEGVSALGMYGEIFRRNTHASGVIPQISLVVGPCAGGAVYSPAITDFTV

MVDQTSHMFITGPDVIKTVTGEDVGFEELGGARTHNAVSGVAHHMAGEE

KDAIEYVKQLLSYLPSNNLSEPPAFPEEADLALTDEDRELDTLVPDSAN

QPYDMHTVIEHILDDAEFLETQPLFAPNILTGFGRVEGHPVGIVANQPM

```
QFAGCLDIDASEKAARFVRTCDAFNVPVITFVDVPGFLPGVGQEHDGII
RRGAKLIYAYAEATVPLITVITRKAFGGAYDVMGSKHLGADLNLAWPTA
QIAVMGAQGAVNILHRRTIAATPEEEREEVRRRLIQEYEDTLLNPYTAA
ERGYIDGVIMPSDTRAHVVRGLRQLRTKRESLPPKKHGNIPL
```

In the present disclosure, trehalose synthase may synthesize trehalose from glucose. The trehalose synthase is, for example, SLI_7555 (SEQ ID NO: 7), sav_7396 (SEQ ID NO: 8), SLI_5710 (SEQ ID NO: 9), sav_2803 (SEQ ID NO: 10) and SLI_6475 (SEQ ID NO: 11) and sav_2151 (SEQ ID NO: 12).

[Sequence 7]
(SEQ ID NO: 7)
```
MTVNEPVPDTFEDTPAGDRHPDWFKRAVFYEVLVRSFQDSNGDGIGDLK
GLTAKLDYLQWLGVDCLWLPPFFKSPLRDGGYDVSDYTAVLPEFGDLAD
FVEFVDAAHQRGMRVIIDFVMNHTSDQHPWFQESRKNPDGPYGDYYVWA
DDDTRYADARIIFVDTEASNWTYDPVRGQYYWHRFFSHQPDLNYENPAV
QEEMLAALKFWLDLGVDGYRLDAVPYLYAEEGTNCENLPASHAFLKRVR
REIDAQYPDTVLLAEANQWPEDVVDYFGDYSTGGDECHMAFHFPVMPRI
FMAVRRESRYPVSEILAKTPAIPSGCQWGIFLRNHDELTLEMVTDEERD
YMYAEYAKDPRMRANIGIRRRLATLLDNDRDQIELFTALLLALPGSPIL
YYGDEIGMGDNIWLGDRDAVRTPMQWTPDRNAGFSTCDPGRLYLPAIMD
PVYGYQVTNVEASMASPSSLLHWTRRMIEIRKQNPAFGLGTYTELPSSN
PAVLAFLREYEDDLVLCVNNFARFAQPTELDLREFAGRHPVELFGGVRF
PAIGELPYLLTLGGHGFYWFRLTRVASRIGRRA
```

[Sequence 8]
(SEQ ID NO: 8)
```
MIVNEPVPDTFEDTPAKDRDPEWFKRAVFYEVLVRSFQDSNGDGVGDLK
GLTAKLDYLQWLGVDCLWLPPFFKSPLRDGGYDVSDYTAVLPEFGDLAD
FVEFVDAAHQRGMRVIIDFVMNHTSDLHPWFQESRSNPDGPYGDYYVWA
DDDKQYQDARIIFVDTEASNWTYDPVRKQYYWHRFFSHQPDLNYESAAV
QEEILAALRFWLDLGIDGFRLDAVPYLYNEEGTNCENLPATHEFLKRVR
KEIDTHYPDTVLLAEANQWPEDVVDYFGDFPSGGDECHMAFHFPVMPRI
FMAVRRESRYPVSEILAKTPAIPSSCQWGIFLRNHDELTLEMVTDEERD
YMWAEYAKDPRMRANIGIRRRLAPLLDNDRNQIELFTALLLSLPGSPIL
YYGDEIGMGDNIWLGDRDAVRTPMQWTPDRNAGFSSCDPGRLYLPTIMD
PVYGYQVTNVEASMSSPSSLLHWTRRMIEIRKGNPAFGLGSYTELQSSN
PAVLAFLREAPSTGGNGDDLVLCVHNFSRFAQPTELDLRAFSGRHPVEL
IGGVRFPAIGELPYLLTLAGHGFYWFRLRKDVTQVTKVSLFVSS
```

[Sequence 9]
(SEQ ID NO: 9)
```
MTVNEPVPDTFEDTPAGDRHPDWFKRAVFYEVLVRSFQDSNGDGIGDLK
GLTAKLDYLQWLGVDCLWLPPFFKSPLRDGGYDVSDYTAVLPEFGDLAD
FVEFVDAAHQRGMRVIIDFVMNHTSDQHPWFQESRRNPDGPYGDYYVWA
DDDKQFQDARIIFVDTEASNWTYDPVRKQYYWHRFFSHQPDLNYENPVV
QEEMISALKFWLDLGIDGFRLDAVPYLYQEEGTNCENLPRTHDFLKRVR
KEIDAQYPDTVVLAEANQWPEDVVDYFGDYAAGGDECHMAFHFPVMPRI
FMAVRRESRYPVSEILAKTPAIPSGCQWGIFLRNHDELTLEMVTDEERD
YMYAEYAKDPRMRANIGIRRRLAPLLDNDRNQIELFTALLLSLPGSPIL
YYGDEIGMGDNIWLGDRDAVRTPMQWTPDRNAGFSSSDPGRLFLPTIMD
PVHGYQVTNVEASMASPSSLLHWTRRMIEIRKQNVAFGLGTYTELPSSN
PAVLAFLREHEDDLVLCVHNFSRFAQPTELDLSAFDGRHPVELFGGVRF
PAVGDLPYLLTLGGHGFYWFRLRKDAA
```

[Sequence 10]
(SEQ ID NO: 10)
```
MIVNEPVPDTFEDTPAKDRDPEWFKRAVFYEVLVRSFQDSNGDGVGDLK
GLTAKLDYLQWLGVDCLWLPPFFKSPLRDGGYDVSDYTAVLPEFGDLAD
FVEFVDAAHQRGMRVIIDFVMNHTSDLHPWFQESRSNPDGPYGDYYVWA
DDDKQYQDARIIFVDTEASNWTFDPVRKGYYWHRFFSHGPDLNYENPAV
QEEIVSALRFWLDLGIDGFRLDAVPYLYQQEGTNCENLPATHEFLKRVR
KEIDTHYPDTVLLAEANQWPEDVVDYFGDFPSGGDECHMAFHFPVMPRI
FMAVRRESRYPVSEILAKTPAIPSSCQWGIFLRNHDELTLEMVTDEERD
YMWAEYAKDPRMRANIGIRRRLAPLLDNDRNQIELFTALLLSLPGSPIL
YYGDEIGMGDNIWLGDRDAVRTPMQWTPDRNAGFSSCDPGRLYLPTIMD
PVYGYQVTNVEASMSSPSSLLHWTRRMIEIRKQNPAFGLGSYTELQSSN
PAVLAFLREAPSTGGNGDDLVLCVHNFSRFAQPTELDLRAFSGRHPVEL
IGGVRFPAIGELPYLLTLAGHGFYWFRLRKDAV
```

[Sequence 11]
(SEQ ID NO: 11)
```
VFMQVWPGEAYPLGATYDGAGTNFAVFTEAADRVELCLLHDDGSETAVE
LRESDAFVRHAYVPGVMPGQRYGYRVHGPYAPERGLRCNSAKLLLLDPYA
RAISGEVQWGEEVYGYHFGAPERRNDLDSAPHTMTSVVVNPYFDWGDDR
RPRTEYHHTVIYEAHVKGLTMRHPGLPEELRGTYAALAHPALIEHLTGL
GVTALELMPVHQFVNDHRLVDMGLNNYWGYNTVGFFAPHNAYASWGDRG
QQVLEFKSAVKALHEAGIEVILDVVYNHTAEGNHLGPTLSFKGLDNPSY
YRLADDPRYYMDTTGTGNSLLMRSPHVLQMIMDSLRYWVTEMHVDGFRF
DLAATLARQFHEVDRLSSFFDLVQQDPWSQVKLIAEPWDVGEGGYQVGN
FPPLWTEWNGKYRDTVRDLWRGEPRTLAEFASRLTGSSDLYQDDGRRPL
ASINFVTCHDGFTLHDMVAYNDKHNHANGEDNRDGESHNRSWNCGVEGD
TDDPAVLELRARQMRNFIATLLLSQGVPMLSHGDEFARTQRGNNNAYCQ
DNELAWVAWPEDGHDLLEFTRAMVWLRKDHPVLRRRRFFHGRPVQGTHD
ELSDIAWFTPEGAEMAQRDWNSARASALTVFLNGNAISEPGTRGERIAD
DSFLLMFNAAPRPLDFVVPVDHGRQWEVVVDTALTAGVPTGTGPKVQAG
DRLTLLDRSLTVLQRPV
```

[Sequence 12]
(SEQ ID NO: 12)
```
MQVWPGEAYPLGATYDGAGTNFAVFSEAAHRIELCLLHDDGSETAVELR
ETDAFVRHAYLPGVMPGQRYGFRVHGPFAPGRGVRCNSAKLLLLDPYAKA
ISGEIKWGEEVYGYHFGAPDKRNDLDSAPHTMTSVVINPYFDWGNDRRP
```

-continued

```
RTEYHHTVLYEAHVKGLTMRHPALPEELRGTYAALAHPAIIEHLTELGV
TALELMPVHQFVNDHRLVDMGLNNYWGYNTIGFFAPHNAYASWGDRGQQ
VLEFKSAVKALHEAGIEVILDVVYNHTAEGNHMGPTLSFKGIDNASYYR
LTDDPRYYMDTTGTGNSLLMRSPHVLGLIMDSLRYWVSDMHVDGFRFDL
AATLARQFHEVDRLSSFFDLVQQDPVVSQVKLIAEPWDVGEGGYQVGNF
PPLWTEWNGKYRDTVRDMWRGEPRTLAEFASRLTGSSDLYQDDGRRPLA
SINFVTCHDGFTLHDLVAYNDKHNQANGEDNRDGESHNRSWNCGAEGDT
```

-continued

```
DDPAVLALRARQMRNFIATLMLSQGVPMLSHGDEFARTQGGNNNAYCQD
GELSWVAWPEDGSELLEFTRAMVWLRRDHPVFRRRRFFHGRPVEGTHDE
LSDIVWFTPTGEEMIQRDWDSAGARALTVFLNGTAISEPGPRGERISDD
SFLLMFNASPKSLEFVVPVDHGRQWQVVVDTARTDGIPPGTVAKVKAGD
RLTLVDRSLTVLQRPA
```

As a specific example, the DNA sequences encoding SEQ ID NO: 1-12 are SEQ ID NO: 13-24, respectively.

[Sequence 13]

(SEQ ID NO: 13)
```
ATGACAGACGCACTCAAGCGCCTCTCCGATGAAGGCGTGGCGATCTGGCTGGACGACCTGT
CGCGCAAGCGGATCACGTCCGGCAACCTCGCCGAGCTGATCGACCAGCAGCACGTCGTGG
GCGTCACCACCAACCCGTCGATCTTCCAGAAGGCCATCTCGCAGGGCGACGGCTACGACC
AGCAGCTCGCCGACCTCGCCGTCCGCGGAGTCACGGTCGAAGAGGCCATCCGCATGATCA
CCACGGCGGACGTCCGCGACGCCGCCGACATCCTGCGCCCCGTCTACGACAACACCGGCG
GCAAGGACGGCCGGGTCTCCATCGAGGTGGACCCGCGGCTGGCGCACAACACCCACGCCA
CGGTGGCCGAGGCCAAGCAGCTGGCGTGGCTGGTGGACCGGCCGAACACCTTCATCAAGA
TCCCGGCGACCGAGGCGGGCCTGCCGGCCATCGCCGAGACCATCGGCCTGGGCATCAGCG
TCAACGTCACGCTGATCTTCTCCCTGGAGCGCTACCGCAAGGTCATGGACGCCTTCCTGAC
CGGCCTGGAGAAGGCCAAGGAGCGTGGCCTGGACCTCTCGCAGATCCACTCCGTGGCGTC
CTTCTTCGTGTCCCGCGTGGACACCGAGATCGACAAGCGGATCGACGCGCTCGGCACCGA
CGAGGCCAAGGCGCAGCGCGGCAAGGCCGCCGTCGCCAACGCCCGCCTGGCCTACCAGGC
GTACGAGGAGGTCTTCGGCACCGACCGCTGGGCCGCCCTGGAGAAGGCCGGCGCCAACAA
GCAGCGTCCGCTGTGGGCGTCGACCGGTGTGAAGGACAAGGCGTACAGCGACACCATGTA
CGTCACCGACCTGGTCGCGCCGAACACGGTCAACACCATGCCGGAGGCCACGCTGCTGGC
CACCGAGGACCACGGCGAGATCACCGGCGACGCCGTCGCCGGGTCGTACGAGCGGGCCCG
CGCGGACCTCGACGCGATCGAGAAGCTCGGGATCTCCTACGACGAGGTGGTCCAGCTCCT
GGAGAAGGAAGGCGTCGACAAGTTCGAGGACGCCTGGAACGACCTGCTGAAGTCCACGGA
GGCGGAGCTCAAGCGCCTCGCTCCCTCGAAGGGCTGA
```

[Sequence 14]

(SEQ ID NO: 14)
```
ATGATCACTGTGACCGAAGCAACCGCCACCGCGGGAGCACTGCAGCGCCTGGCCGACCAG
GGCGTGTCCGTCTGGCTCGACGACCTGTCGCGGCGGCGGATCGAGTCCGGCAACCTCGCC
GAGCTGATCAGGACGAAGAACGTCGTCGGAGTCACCACCAACCCGTCGATCTTCCAGGCCG
CCATAGGCTCCGGCGAGGGCTACGAGGAGCAGCTCGCCGACCTGGCGACCCGGGGCGTCA
CCGTCGACGAGGCGGTCCGCATGATGACCACCGCCGATGTCCGCGCCGCCGCCGACGTGC
TGCGCGGGGTGTACGACGCCTCCGGCGGGCGCGACGGCCGCGTCTCCATCGAGGTCGACC
CGCGCCTGGCCCACGACACGGCGGCGACGGTCGCCGAGGCCCGCCAGCTGTCCTGGCTGG
TCGACCGTCCCAACGTGATGATCAAGATCCCGGCGACGAAGGCCGGTCTCCCGGCCATCAC
CGAGGTCATCGGCGCCGGCATCAGTGTGAACGTCACGCTGATCTTCTCCCTGGAGCGCTAC
CGCGAGGTCATGGACGCCTACCTCGCCGGCCTGGAGAAGGCGCAGGCGGCCGGGATCGAC
CTGGCCGGCATCCACTCGGTCGCGTCCTTCTTCGTCTCCCGCGTCGACAGCGAGATCGACA
```

-continued

AGCGCCTGTCCCTGCTGGGCACCGAAGAGGCGCTCGGCCTGCGCGGCCGGGCGGCACTGG

CCAACGCACGACTGGCCTACGAGGCGTACGAGAACGTCTTCGCGGGCGACCGCTTCACCG

CCCTCGCGGGGCCCGCGCGAACCCCCAGCGCCCCCTGTGGGCGTCCACCGGTGTGAAGG

ACCCGGCATTCCGGGACACCCTGTACGTGGAGGAGCTGGTCGCCCCCGGCACCGTGAACA

CGATGCCGGAGGCCACCCTGGACGCCGCCGCCGATCACGGCGACGTACGGGGCGACACGG

TCACCGGCGGGTACGCCCAGGCCCGCGCCGATCTCGCGGCCGTGGAGCGGCTCGGCGTGT

CGTACGACGAGGTGGTGGAGCAGTTGGAGCAGGAGGGCGTGGCGAAGTTCGAGGCGGCCT

GGCAGGAGCTGCTCGCCGCCGTGACGAAGTCCCTCGACAGCAAGGGAGTTGACGGGGAAT

GA

[Sequence 15]
(SEQ ID NO: 15)
ATGACAGACGCACTCAAGCGCCTCTCCAAGGAAGGCGTCGCGATCTGGCTGGACGACCTGT

CGCGCAAGCGGATCACGTCCGGCAACCTCGCCGAACTGATCGACCAGCAGCACGTCGTGG

GCGTCACCACCAACCCGTCGATCTTCCAGAAGGCCATCTCTCAGGGCGACGGTTACGACCA

GCAGGTCTCCGACCTCGCCGCCCGCCGGGTCACCGTCGAAGAAGCCATCCGCATGATCAC

CACGGCGGACGTCCGCGACGCCGCCGACATCCTGCGCCCGGTCTTCGACGCCACCGACGG

CCAGGACGGCCGGGTCTCGATCGAGGTCGACCCGCGCCTGGCCCACAACACCAAGGCGAC

GGTCGCCGAGGCCAAGCAGCTGGCCTGGCTGGTCGACCGCCCCAACACGCTCATCAAGAT

CCCGGCCACCAAGGCGGGCATCCCGGCGATCACGGAGGTCATCGGCCTCGGCATCAGCGT

CAACGTGACGCTGATCTTCTCGCTCGAGCGCTACCGCATGGTCATGGACGCCTACCTCGCC

GGCCTGGAGAAGGCCAAGGAGCGCGGCCTGGACCTGTCGAAGATCCACTCGGTGGCGTCC

TTCTTCGTGTCCCGCGTGGACACCGAGATCGACAAGCGGATCGACGCCCTCGGCACGCCG

GAGGCCAAGGCCGCGCGCGGCAAGGCGGGCCTCGCCAACGCCCGGCTCGCCTACGAGGC

GTACGAGGCGGTCTTCTCCACCGACCGCTGGCTCGCCCTCGACAAGGCGCAGGCCAACAA

GCAGCGCCCGCTGTGGGCCTCCACCGGCGTCAAGGACCCGGCGTACAAGGACACCATGTA

CGTCGAGGAACTGGTCGCGCCGAACACCGTGAACACCATGCCGGAGGCCACTTTGGAGGC

CACCGCGGACCACGGCGAGATCCGGGCAACACCATCGCCGGCACGTACGAGCAGGCCCG

CGCCGACCTCGACGCCGTCGAGAAGCTCGGGATCGCGTACGACGACGTGGTCCAGCTCCT

GGAGGAAGAGGGCGTCGACAAGTTCGAGGCGTCCTGGAACGACCTGCTCAAGTCGACCGA

GGCGGAGCTCCAGCGCCTCGCCCCCTCGGAGGGCTGA

[Sequence 16]
(SEQ ID NO: 16)
ATGATCACTGTGAGCAACACCGTCGAAAACCTCGAGCGCCTCTCCGACGAAGGCGTCTCCA

TCTGGCTGGACGATCTGTCGCGCAAGCGGATCACGTCCGGCAACCTCGCCGAACTCATCGC

GCACAAGCACGTGGTGGGCGTCACCACCAACCCGTCCATCTTCCAGGCCGCCATCGGCTC

CGGAGAGGGATACGAGGAGCAGCTGGCCGATCTGGCCGTGCGTGGCGTCACGGTCGACGA

GGCCGTGCGCATGATGACGACCGCCGACGTGCGCGCCGCCGCCGACATCCTGCGGCCCGT

GTACGACGCGACCGGCGGCCGTGACGGCCGGGTCTCCATCGAGGTCGACCCGCGCCTCGC

CCACGACACCGAGGCGACGATCGCCGAAGCCAAGCAGCTCGCCTGGCTGGTGGACCGCCC

CAACGTGATGATCAAGATTCCGGCGACCAAGGCCGGTCTCCCCGCGATCACCGAGGTCATC

GGCCTCGGCATCAGCGTCAACGTCACGCTGATCTTCTCGCTCGAGCGCTACCGCGAGGTGA

TGGACGCCTACCTCGCCGGTCTGGAGCGGGCGCAGGCCGCGGGCATCGACCTGGCCGGCA

TCCACTCCGTCGCCTCCTTCTTCGTCTCCCGCGTCGACAGCGAGATCGACAAGCGCCTGGC

-continued

GAAGGCCGGCACGGACGACGCGCAGGCCCTCAAGGGCAAGGCGGCGCTCGCCAACGCCCG

GCTCGCGTACGAGGCGTACGAAGAGGTCTTCGCCGGGGAGCGCTGGACCGCGCTCGCCCC

GGCCGGCGCGCACAAGCAGCGTCCGCTGTGGGCCTCGACGGGCGTGAAGGACCCGGCGTA

CAAGGACACCCTGTACGTCGACGAGCTGGTCGCTCCCGGCACGGTCAACACCATGCCGGA

GGGGACCTTGAACGCCACCGCCGACCACGGCGACATCCACGGCGACACGGTGACCGGCGG

CTATGCCCAGGCCCGCGCCGACCTGGCCGCCGTGGAGCGGCTGGGGATCTCGTACGACGA

GGTCGTGAAGCAGCTGGAGGAGGAGGCCGTCGCCAAGTTCGAGGTGGCGTGGGGCGACCT

GCTGGAGGCCGTCGCGACCTCGCTGCGCGGCAAGGGAGCTGACGGCGAATGA

[Sequence 17]
                                                   (SEQ ID NO: 17)
ATGTCCGAGCCGGAAGAGCAGCAGCCCGACATCCACACGACCGCGGGCAAGCTCGCGGAT

CTCAGGCGCCGTATCGAGGAAGCGACGCACGCCGGTTCCGCACGCGCCGTCGAGAAACAG

CACGCCAAGGGCAAGCTGACGGCTCGTGAGCGCATCGACCTCCTCCTCGACGAGGGCTCC

TTCGTCGAGCTGGACGAGTTCGCCCGGCACCGCTCCACCAACTTCGGCCTCGACGCCAAC

CGCCCTTACGGCGACGCGTCGTCACCGGTTACGGCACCGTCGACGCCGCCCCGTGGCC

GTCTTCTCCCAGGACTTCACCGTCTTCGGCGGCGCGCTGGGCGAGGTCTACGGCCAGAAGA

TCGTCAAGGTGATGGACTTCGCGCTGAAGACCGGCTGCCCGGTCGTCGGCATCAACGACTC

CGGCGGCGCCCGCATCCAGGAGGGCGTGGCCTCCCTCGGCGCCTACGGCGAGATCTTCCG

CCGCAACACCCACGCCTCCGGCGTGATCCCGCAGATCAGCCTGGTCGTCGGCCCGTGCGC

GGGCGGCGCGGTCTACTCCCCCGCGATCACCGACTTCACGGTGATGGTCGACCAGACCAG

CCACATGTTCATCACCGGCCCCGACGTCATCAAGACGGTCACCGGTGAGGACGTCGGCTTC

GAGGAGCTGGGCGGCGCCCGCACCCACAACACCGCCTCGGGCGTGGCCCACCACATGGCG

GGTGACGAGAAGGACGCCGTCGAGTACGTCAAGCAGCTCCTGTCGTACCTGCCGTCCAACA

ACCTGTCCGAGCCCCCCGCCTTCCCGGAGGAGGCGGACCTCGCGGTCACGGACGAGGACG

CCGAGCTGGACGCGATCGTCCCGGACTCGGCGAACCAGCCCTACGACATGCACAGCGTCA

TCGAGCACGTCCTGGACGACGGCGAGTTCTTCGAGACCCAGCCCCTGTTCGCACCGAACAT

CCTCACCGGCTTCGGCCGCGTGGAGGGCCGCCCGGTCGGCATCGTCGCCAACCAGCCCAT

GCAGTTCGCCGGGTGCCTGGACATCACCGCCTCCGAGAAGGCGGCCCGCTTCGTGCGCAC

CTGCGACGCCTTCAACGTCCCCGTGCTCACCTTCGTGGACGTCCCCGGCTTCCTGCCCGGC

GTCGACCAGGAGCACGACGGCATCATCCGCCGCGGCGCCAAGCTGATCTTCGCCTACGCC

GAGGCCACGGTGCCGCTGATCACGGTCATCACCCGCAAGGCCTTCGGCGGCGCCTACGAC

GTCATGGGCTCCAAGCACCTGGGCGCCGACCTCAACCTGGCCTGGCCCACCGCCCAGATC

GCCGTCATGGGCGCCCAGGGCGCGGTCAACATCCTGCACCGCCGCACCATCGCCGACGCC

GGTGACGACGCCGAGGCCACCCGGGCCCGCCTGATCCAGGAGTACGAGGACGCCCTCCTC

AACCCCTACACGGCGGCCGAACGCGGCTACGTCGACGCCGTGATCATGCCCTCCGACACT

CGCCGCCACATCGTCCGCGGCCTGCGCCAGCTACGCACCAAGCGCGAGTCCCTGCCCCCG

AAGAAGCACGGCAACATCCCCCTGTAA

[Sequence 18]
                                                   (SEQ ID NO: 18)
ATGTCCGAGCCGGAAGAGCTGCACCACCCCGATATCCACACCACCGCGGGCAAACTCGCG

GATCTGCAGCGCCGCATCCAGGAGGCGACGCACGCCGGCTCGGAGCGCGCCGTCGAAAAG

CAGCACGCCAAGGGCAAGCTGACGGCCCGTGAGCGGATCGCGCTGCTGCTCGACGAGGAC

-continued

```
TCCTTCGTCGAGCTGGACGAGTTCGCGCAGCACCGCTCCACGGACTTCGGCATGGAGAACA
ACCGCCCGTACGGAGACGGTGTCGTCACCGGGTACGGGACCGTGGACGGCCGCCCCGTCG
CCGTGTTCTCGCAGGACTTCACCGTCTTCGGCGGTGCCCTCGGCGAGGTCTTCGGGCAGAA
GATCATGAAGGCGATGGACTTCGCCCTGAAGACGGGCTGTCCGGTCATCGGCATCAACGAC
TCCGGCGGCGCCCGTATCCAGGAGGGCGTCTCGGCCCTCGGCATGTACGGCGAGATCTTC
CGCCGCAACACCCATGCCTCGGGCGTGATCCCGCAGATCAGCCTGGTCGTCGGCCCGTGC
GCGGGCGGCGCGGTCTACTCCCCCGCGATCACCGACTTCACGGTGATGGTCGACCAGACC
TCGCACATGTTCATCACGGGCCCCGACGTCATCAAGACGGTGACGGGCGAGGACGTCGGCT
TCGAGGAGCTGGGCGGCGCCCGCACGCACAACGCGGTGTCGGGCGTGGCCCATCACATGG
CGGGGGAGGAGAAGGACGCGATCGAGTACGTCAAGCAGCTGCTGTCGTACCTGCCGTCCA
ACAACCTCAGCGAGCCGCCGGCCTTCCCGGAGGAGGCGGACCTCGCCCTCACCGACGAGG
ACCGCGAGCTGGACACCCTCGTACCCGACAGTGCGAACCAGCCGTACGACATGCACACGG
TGATCGAACACATCCTGGACGACGCCGAGTTCCTGGAGACGCAGCCGCTGTTCGCGCCGAA
CATCCTCACCGGCTTCGGCCGGGTCGAGGGCCACCCGGTGGGCATCGTCGCCAACCAGCC
GATGCAGTTCGCGGGCTGCCTCGACATCGACGCGTCCGAGAAGGCCGCCCGCTTCGTGCG
CACCTGCGACGCGTTCAACGTCCCGGTGATCACTTTCGTGGACGTGCCGGGCTTCCTGCCC
GGTGTCGGCCAGGAGCACGACGGCATCATCCGCCGCGGCGCCAAGCTGATCTACGCGTAC
GCCGAGGCGACCGTCCCGCTGATCACCGTCATCACCCGCAAGGCGTTCGGCGGCGCGTAC
GACGTCATGGGCTCCAAGCACCTGGGCGCCGACCTCAACCTCGCCTGGCCGACCGCCCAG
ATCGCCGTGATGGGCGCGCAGGGCGCGGTCAACATCCTGCACCGCCGCACCATCGCCGCC
ACACCCGAGGAGGAGCGCGAGGAGGTCCGCCGGCGGCTCATCCAGGAGTACGAGGACACG
CTGCTCAACCCCTACACGGCGGCCGAGCGCGGCTACATCGACGGCGTGATCATGCCGTCC
GACACCCGCGCCCATGTCGTACGGGGCTGCGTCAGCTCCGTACGAAGCGGGAATCCCTG
CCTCCGAAGAAGCACGGCAACATCCCCCTCTAG
```

[Sequence 19]
(SEQ ID NO: 19)
```
ATGACCGTCAACGAGCCCGTACCTGACACCTTCGAGGACACCCCCGCGGGGACCGGCAC
CCGGACTGGTTCAAACGAGCCGTCTTCTACGAGGTCCTCGTCCGCTCCTTCCAGGACAGCA
ACGGCGACGGCATCGGTGATCTCAAGGGCCTGACCGCCAAGCTGGACTACCTGCAATGGCT
CGGCGTGGACTGCCTGTGGCTCCCGCCCTTCTTCAAGTCACCGCTGCGCGACGGCGGTTAC
GACGTCTCCGACTACACCGCCGTGCTGCCGGAGTTCGGCGACCTGGCCGACTTCGTGGAGT
TCGTGGACGCGGCGCACCAGCGCGGCATGCGCGTGATCATCGACTTCGTCATGAACCACAC
CAGCGACCAGCACCCGTGGTTCCAGGAGTCCCGCAAGAACCCGGACGGCCCCTACGGCGA
CTACTACGTCTGGGCCGACGACGACACCCGGTACGCCGACGCCCGCATCATCTTCGTCGAC
ACCGAGGCCTCCAACTGGACCTACGACCCGGTCCGCGGCCAGTACTACTGGCACCGGTTCT
TCTCCCACCAGCCGGACCTCAACTACGAGAACCCGGCCGTGCAGGAGGAGATGCTCGCCG
CCCTGAAGTTCTGGCTGGACCTGGGCGTGGACGGCTACCGTCTCGACGCCGTGCCCTACCT
GTACGCCGAGGAGGGCACCAACTGCGAGAACCTGCCCGCCTCCCACGCGTTCCTCAAGCG
GGTGCGCCGCGAGATCGACGCACAGTACCCGGACACCGTACTGCTGGCCGAGGCCAACCA
GTGGCCGGAGGACGTGGTCGACTACTTCGGCGACTACTCCACGGGCGGCGACGAGTGCCA
CATGGCCTTCCACTTCCCCGTCATGCCCCGCATCTTCATGGCCGTGCGCCGCGAGTCCCGC
TACCCGGTCTCCGAAATCCTCGCCAAGACCCCCGCGATCCCGTCCGGCTGCCAGTGGGGC
```

-continued

ATCTTCCTGCGCAACCACGACGAGCTGACCCTGGAGATGGTCACCGACGAGGAACGCGACT

ACATGTACGCGGAGTACGCCAAGGACCCGCGCATGCGCGCCAACATCGGTATCCGCCGGC

GGCTGGCCACCCTGCTGGACAACGACCGCGACCAGATCGAGCTGTTCACCGCCCTGCTGC

TCGCCCTCCCGGGATCCCCGATCCTCTACTACGGCGACGAGATCGGCATGGGCGACAACAT

CTGGCTCGGCGACCGCGACGCCGTGCGCACCCCCATGCAGTGGACGCCCGACCGCAACGC

CGGCTTCTCGACCTGTGACCCGGGCCGCCTCTACCTGCCCGCGATCATGGACCCGGTCTAC

GGCTACCAGGTGACGAACGTCGAGGCGTCCATGGCCTCGCCCTCCTCCCTGCTGCACTGGA

CCCGGCGCATGATCGAGATCCGCAAGCAGAACCCGGCCTTCGGCCTCGGCACCTACACCG

AACTGCCCTCCTCCAACCCGGCGGTGCTCGCCTTCCTGCGGGAGTACGAGGACGACCTGGT

GCTGTGTGTGAACAACTTCGCACGGTTCGCCCAGCCCACCGAGCTGGATCTGCGCGAGTTC

GCCGGACGCCATCCGGTCGAGCTGTTCGGCGGGGTCCGCTTCCCCGCCATCGGCGAACTG

CCGTACCTGCTGACCCTCGGGGGCCACGGCTTCTACTGGTTCCGGCTCACCCGAGTCGCAT

CCCGCATCGGCCGCCGCGCTTGA

[Sequence 20]

(SEQ ID NO: 20)
ATGATCGTCAACGAGCCCGTCCCGGACACCTTCGAGGACACGCCCGCCAAGGACGCGAT

CCGGAGTGGTTCAAACGCGCCGTCTTCTACGAGGTCCTGGTCCGCTCCTTCCAGGACAGCA

ACGGCGACGGTGTCGGCGACCTGAAGGGCCTGACCGCCAAGCTGGACTATCTGCAGTGGC

TGGGCGTGGACTGCCTGTGGCTGCCGCCGTTCTTCAAGTCCCCCCTGCGCGACGGCGGCT

ACGACGTCTCCGACTACACCGCGGTGCTGCCCGAGTTCGGTGACCTGGCCGACTTCGTCGA

GTTCGTGGACGCGGCCCACCAGCGCGGCATGCGCGTGATCATCGACTTCGTGATGAACCAC

ACCAGTGACCTGCATCCGTGGTTCCAGGAGTCCCGCAGCAACCCCGACGGCCCCTACGGC

GACTACTACGTGTGGGCCGACGACGACAAGCAGTACCAGGACGCCCGGATCATCTTCGTCG

ACACCGAGGCCTCCAACTGGACGTACGACCCGGTCCGCAAGCAGTACTACTGGCACCGCTT

CTTCTCCCACCAGCCCGACCTCAACTACGAGAGTGCCGCCGTCCAGGAGGAGATCCTGGC

GGCGCTGCGGTTCTGGCTCGATCTGGGCATCGACGGCTTCAGGCTGGACGCCGTCCCCTAC

CTGTACAACGAAGAGGGGACGAACTGCGAGAACCTGCCGGCGACGCACGAGTTCCTGAAG

CGGGTGCGCAAGGAGATCGACACGCACTATCCGGACACGGTGCTGCTCGCGGAGGCGAAC

CAGTGGCCGGAGGACGTGGTCGACTACTTCGGCGACTTCCCCTCGGGCGGCGACGAGTGC

CACATGGCGTTCCATTTCCCGGTCATGCCGCGGATCTTCATGGCGGTGCGGCGTGAGTCGC

GGTATCCGGTGTCGGAGATCCTGGCGAAGACGCCGGCGATCCCGTCGAGCTGCCAGTGGG

GCATCTTCCTGCGCAACCACGACGAGCTGACCCTGGAGATGGTCACCGACGAGGAACGCG

ACTACATGTGGGCGGAGTACGCCAAGGATCCGCGGATGCGGGCCAACATCGGCATCCGCC

GGCGTCTGGCGCCGCTGCTGGACAACGACCGCAACCAGATCGAGCTGTTCACCGCGCTGC

TGCTGTCGCTGCCCGGCTCGCCGATCCTCTACTACGGCGACGAGATCGGGATGGGGACAA

CATCTGGCTCGGTGACCGGGACGCGGTGCGCACGCCGATGCAGTGGACGCCGGACCGCAA

CGCGGGTTTCTCGTCCTGCGACCCGGGGCGTCTGTATCTGCCCACGATCATGGATCCGGTC

TACGGGTACCAGGTCACGAACGTGGAGGCGTCGATGTCGTCGCCGTCCTCGCTGCTGCACT

GGACCCGGCGGATGATCGAGATCCGTAAGCAGAACCCGGCGTTCGGCCTCGGCTCGTACA

CCGAACTCCAGTCCTCGAACCCGGCCGTCCTCGCGTTCCTGCGGGAGGCCCCCTCGACCG

GGGGGAACGGGGACGACCTGGTGCTGTGCGTGCACAACTTCTCCCGGTTCGCGCAGCCCA

-continued

CGGAGCTGGATCTGCGGGCGTTCAGCGGCCGTCATCCGGTCGAGCTGATCGGCGGTGTCC

GCTTCCCGGCCATCGGGGAACTCCCGTATCTGCTGACCCTGGCAGGCCACGGCTTCTACTG

GTTCCGGCTCCGCAAGGACGTCACCCAGGTCACCAAGGTGAGCTTGTTCGTGAGCTCTTGA

[Sequence 21]

(SEQ ID NO: 21)
ATGACCGTCAACGAGCCCGTACCTGACACCTTCGAGGACACCCCCGCGGGGGACCGGCAC

CCGGACTGGTTCAAACGAGCCGTCTTCTACGAGGTCCTCGTCCGCTCCTTCCAGGACAGCA

ACGGCGACGGCATCGGTGATCTCAAGGGCCTGACCGCCAAGCTGGACTACCTGCAATGGCT

CGGCGTGGACTGCCTGTGGCTCCCGCCCTTCTTCAAGTCACCGCTGCGCGACGGCGGTTAC

GACGTCTCCGACTACACCGCCGTGCTGCCGGAGTTCGGCGACCTGGCCGACTTCGTGGAGT

TCGTGGACGCGGCGCACCAGCGCGGCATGCGCGTGATCATCGACTTCGTCATGAACCACAC

CAGCGACCAGCACCCGTGGTTCCAGGAGTCCCGCAGGAACCCGGACGGCCCCTACGGCGA

CTACTACGTCTGGGCCGACGACGACAAGCAGTTCCAGGACGCGCGGATCATCTTCGTCGAC

ACCGAGGCGTCCAACTGGACCTACGACCCGGTGCGCAAGCAGTACTACTGGCACCGGTTCT

TCTCCCACCAGCCGGACCTCAACTACGAGAACCCGGTCGTGCAGGAGGAGATGATCTCCGC

GCTGAAGTTCTGGCTGGACCTGGGCATCGACGGGTTCCGGCTGGACGCGGTGCCGTACCTC

TACCAGGAGGAGGGCACCAACTGCGAGAACCTCCCGCGCACGCACGACTTCCTGAAGCGG

GTGCGCAAGGAGATCGACGCGCAGTACCCGGACACGGTGGTGCTGGCCGAGGCCAACCAG

TGGCCGGAGGACGTGGTCGACTACTTCGGCGACTACGCGGCGGGCGGCGACGAGTGCCAC

ATGGCCTTCCACTTCCCCGTCATGCCCCGCATCTTCATGGCGGTCAGAAGGGAGTCCCGCT

ACCCGGTCTCCGAAATCCTCGCCAAGACCCCGGCCATCCCGTCCGGCTGCCAGTGGGGCA

TCTTCCTGCGCAACCACGACGAGCTGACCCTGGAGATGGTCACCGACGAGGAACGCGACTA

CATGTACGCGGAGTACGCCAAGGACCCGCGCATGCGCGCCAACATCGGCATCCGGCGCAG

GCTCGCCCCGCTCCTCGACAACGACCGCAACCAGATCGAGCTGTTCACCGCCCTGCTGCTG

TCCCTGCCCGGCTCGCCGATCCTCTACTACGGCGACGAGATCGGCATGGGCGACAACATCT

GGCTCGGCGACCGCGACGCCGTGCGCACCCCCATGCAGTGGACGCCCGACCGCAACGCGG

GCTTCTCGTCGTCCGACCCGGGCCGCCTGTTCCTGCCCACGATCATGGACCCGGTCCACG

GTTACCAGGTGACGAACGTCGAGGCGTCCATGGCCTCGCCCTCCTCCCTGCTGCACTGGAC

CCGGCGCATGATCGAGATCCGCAAGCAGAACGTGGCCTTCGGCCTGGGCACCTACACCGA

GCTGCCGTCGTCCAACCCTGCCGTCCTGGCCTTCCTGCGCGAACACGAGGACGACCTGGT

GCTGTGCGTCCACAACTTCTCCCGGTTCGCGCAGCCGACGGAGCTGGACCTCAGCGCCTTC

GACGGACGCCATCCGGTCGAGCTGTTCGGCGGGGTCCGCTTCCCGGCGGTCGGTGACCTG

CCGTACCTGCTGACCCTGGGCGGTCACGGCTTCTACTGGTTCCGCCTGCGCAAGGACGCCG

CCTGA

[Sequence 22]

(SEQ ID NO: 22)
ATGATCGTCAACGAGCCCGTCCCGGACACCTTCGAGGACACGCCCGCCAAGGACCGCGAT

CCGGAGTGGTTCAAACGCGCCGTCTTCTACGAGGTCCTGGTCCGCTCCTTCCAGGACAGCA

ACGGCGACGGTGTCGGCGACCTGAAGGGCCTGACCGCCAAGCTGGACTATCTGCAGTGGC

TGGGCGTGGACTGCCTGTGGCTGCCGCCGTTCTTCAAGTCCCCCCTGCGCGACGGCGGCT

ACGACGTCTCCGACTACACCGCGGTGCTGCCCGAGTTCGGTGACCTGGCCGACTTCGTCGA

GTTCGTGGACGCGGCCCACCAGCGCGGCATGCGCGTGATCATCGACTTCGTGATGAACCAC

ACCAGCGACCTGCACCCGTGGTTCCAGGAGTCCCGCAGCAACCCCGACGGCCCCTACGGC

-continued

GACTACTACGTGTGGGCCGACGACGACAAGCAGTACCAGGACGCCCGGATCATCTTCGTCG
ACACCGAGGCCTCCAACTGGACCTTCGACCCGGTCCGCAAGCAGTACTACTGGCACCGCTT
CTTCTCCCACCAGCCCGACCTCAACTACGAGAACCCGGCGGTGCAGGAGGAGATCGTCTCC
GCCCTGCGGTTCTGGCTCGACCTCGGCATCGACGGCTTCCGCCTCGACGCGGTGCCGTAC
CTGTACCAGCAGGAAGGCACCAACTGCGAGAACCTGCCGGCGACGCACGAGTTCCTGAAG
CGGGTGCGCAAGGAGATCGACACGCACTATCCGGACACGGTGCTGCTCGCGGAGGCGAAC
CAGTGGCCGGAGGACGTGGTCGACTACTTCGGCGACTTCCCCTCGGGCGGCGACGAGTGC
CACATGGCGTTCCATTTCCCGGTCATGCCGCGGATCTTCATGGCGGTGCGGCGTGAGTCGC
GGTATCCGGTGTCGGAGATCCTGGCGAAGACGCCGGCGATCCCGTCGAGCTGCCAGTGGG
GCATCTTCCTGCGCAACCACGACGAGCTGACCCTGGAGATGGTCACCGACGAGGAACGCG
ACTACATGTGGGCGGAGTACGCCAAGGATCCGCGGATGCGGGCCAACATCGGCATCCGCC
GGCGTCTGGCGCCGCTGCTGGACAACGACCGCAACCAGATCGAGCTGTTCACCGCGCTGC
TGCTGTCGCTGCCCGGCTCGCCGATCCTCTACTACGGCGACGAGATCGGCATGGGGGACAA
CATCTGGCTCGGTGACCGGGACGCGGTGCGCACTCCGATGCAGTGGACGCCGGACCGCAA
CGCGGGTTTCTCGTCCTGCGACCCGGGGCGTCTGTATCTGCCCACGATCATGGATCCGGTC
TACGGGTACCAGGTCACGAACGTGGAGGCGTCGATGTCGTCGCCGTCCTCGCTGCTGCACT
GGACCCGGCGGATGATCGAGATCCGTAAGCAGAACCCGGCGTTCGGCCTCGGCTCGTACA
CCGAACTCCAGTCCTCGAACCCGGCCGTCCTCGCGTTCCTGCGGGAGGCCCCCTCGACCG
GGGGGAACGGGGACGACCTGGTGCTGTGCGTGCACAACTTCTCCCGGTTCGCGCAGCCCA
CGGAGCTGGATCTGCGGGCGTTCAGCGGCCGTCATCCGGTCGAGCTGATCGGCGGTGTCC
GCTTCCCGGCCATCGGGGAACTCCCGTATCTGCTGACCCTGGCAGGCCACGGCTTCTACTG
GTTCCGGCTCCGCAAGGACGCCGTCTAG

[Sequence 23]
(SEQ ID NO: 23)
GTGTTCATGCAGGTCTGGCCTGGAGAGGCGTATCCACTGGGTGCCACGTACGACGGCGCCG
GCACCAACTTCGCGGTCTTCACGGAGGCCGCCGACCGAGTAGAGCTGTGTCTGCTGCACGA
CGACGGTTCGGAGACGGCGGTCGAGCTGCGGGAGAGCGATGCCTTCGTGCGGCACGCGTA
CGTGCCGGGCGTGATGCCGGGGCAGCGGTACGGCTACCGCGTGCACGGCCCGTACGCCCC
GGAGCGCGGACTGCGCTGCAACAGCGCCAAGCTGCTCCTCGATCCGTACGCGCGTGCGAT
CAGCGGGGAGGTCCAGTGGGGCGAGGAGGTGTACGGCTACCACTTCGGCGCACCCGAACG
GCGCAACGACCTCGACTCGGCCCCGCACACGATGACGTCGGTCGTGGTCAACCCGTACTTC
GACTGGGGCGACGACCGGCGCCCCCGTACGGAGTACCACCACACGGTGATCTACGAGGCC
CACGTGAAGGGCCTGACCATGCGCCACCCGGGCCTGCCCGAGGAGCTGCGGGGCACCTAC
GCGGCCCTCGCGCACCCGGCGCTCATCGAGCACCTCACGGGGCTCGGGGTGACCGCGCTG
GAGCTGATGCCGGTCCATCAGTTCGTCAACGACCACCGGCTGGTGGACATGGGCCTCAACA
ACTACTGGGGCTACAACACGGTCGGGTTCTTCGCCCCGCACAACGCCTACGCCTCCTGGGG
CGACCGCGGCCAGCAGGTGCTGGAGTTCAAGTCCGCGGTCAAGGCGCTGCACGAGGCGGG
GATCGAGGTGATCCTCGACGTGGTCTACAACCACACCGCGGAGGGCAACCACCTGGGCCC
GACGCTGTCCTTCAAGGGGCTGGACAACCCCTCGTACTACCGGCTGGCCGACGACCCCCG
CTACTACATGGACACCACGGGGACCGGGAACTCGCTGCTCATGCGGTCCCCGCACGTACTC
CAGATGATCATGGACTCACTGCGGTACTGGGTCACCGAGATGCACGTGGACGGGTTCCGTT -continued

```
TCGACCTCGCGGCCACGCTGGCCCGGCAGTTCCACGAGGTGGACCGGCTGTCGTCGTTCTT

CGACCTGGTGCAGCAGGACCCCGTGGTCTCGCAGGTGAAGCTGATCGCCGAGCCGTGGGA

CGTGGGCGAGGGCGGCTACCAGGTGGGCAACTTCCCGCCGCTGTGGACCGAGTGGAACGG

CAAGTACCGGGACACGGTGCGGGACCTGTGGCGCGGCGAGCCGCGCACGCTGGCGGAGTT

CGCGTCCCGGCTGACCGGTTCCTCCGACCTCTACCAGGACGACGGGCGCCGCCCGCTGGC

CTCGATCAACTTCGTGACCTGCCACGACGGCTTCACCCTGCACGACATGGTGGCCTACAAC

GACAAGCACAACCACGCCAACGGCGAGGACAACCGGGACGGCGAGAGCCACAACCGTTCC

TGGAACTGCGGTGTCGAGGGCGACACCGACGATCCGCGGTGCTGGAGCTGCGGGCGCGG

CAGATGCGCAACTTCATCGCCACGCTGCTGCTCTCCCAGGGCGTCCCGATGCTCAGCCACG

GCGACGAGTTCGCCCGCACCCAGCGGGGCAACAACAACGCCTACTGCCAGGACAACGAGC

TGGCGTGGGTGGCGTGGCCCGAGGACGGCCACGACCTCCTGGAGTTCACCCGCGCGATGG

TCTGGCTGCGCAAGGACCACCCGGTCCTGCGCAGGCGCCGCTTCTTCCACGGGCGCCCGG

TGCAGGGCACCCACGACGAGCTGTCGGACATCGCCTGGTTCACGCCGGAGGGCGCGGAGA

TGGCCCAGCGGGACTGGAACTCGGACGCACGGGCCTCCGCGCTCACGGTCTTCCTGAACGGCA

ACGCGATCTCCGAGCCCGGCACCCGCGGGGAACGCATCGCCGACGATTCGTTCCTGCTGA

TGTTCAACGCCGCGCCGAGGCCGCTGGACTTCGTGGTGCCGGTCGATCACGGCCGGCAGT

GGGAGGTGGTCGTCGACACCGCTCTGACGGCCGGGGTGCCCACGGGCACGGGCCCGAAGG

TGCAGGCCGGGGACCGGCTGACCCTCCTGGACCGGAGCCTGACGGTGTTGCAGCGGCCGG

TGTAG
```

[Sequence 24]
(SEQ ID NO: 24)
```
ATGCAGGTCTGGCCTGGAGAGGCATATCCACTCGGCGCCACGTACGACGGCGCCGGTACC

AATTTCGCGGTCTTCTCGGAGGCCGCCCATCGGATCGAGCTGTGTCTGCTGCACGACGACG

GCTCGGAGACGGCGGTGGAACTGAGGGAGACCGACGCGTTCGTGCGGCACGCGTATCTGC

CCGGCGTCATGCCGGGGCAGCGGTACGGCTTCCGCGTGCACGGCCCGTTCGCGCCGGGGC

GCGGGGTGCGCTGCAATTCCGCCAAGCTGCTGCTCGATCCGTACGCGAAGGCGATCAGCG

GCGAGATCAAGTGGGGCGAGGAGGTGTACGGCTACCACTTCGGCGCCCCCGACAAGCGCA

ACGACCTGGACTCGGCGCCGCACACGATGACCTCGGTCGTGATCAACCCGTACTTCGACTG

GGGCAACGACCGGCGGCCGCGCACCGAGTACCACCACACAGTGCTCTACGAGGCCCATGT

GAAGGGCCTGACGATGCGGCATCCCGCGCTGCCCGAGGAACTGCGCGGCACGTATGCGGC

GCTCGCCCACCCCGCCATCATCGAACACCTGACTGAACTGGGCGTCACCGCGCTCGAACT

GATGCCGGTGCACCAGTTCGTGAACGACCACCGTCTGGTGGACATGGGCCTGAACAACTAC

TGGGGCTACAACACGATCGGTTTCTTCGCCCCGCACAACGCGTACGCCTCCTGGGGCGACC

GCGGCCAGCAGGTGCTGGAGTTCAAGTCGGCAGTGAAGGCGCTGCACGAGGCCGGGATCG

AGGTCATCCTGGACGTGGTCTACAACCACACGGCCGAGGGCAACCACATGGGCCCGACGC

TCTCCTTCAAGGGCATCGACAACGCGTCGTACTACCGGCTCACCGACGATCCCCGCTACTA

CATGGACACCACGGGGACCGGGAACTCCCTCCTCATGCGCTCCCCGCACGTCCTCCAACT

GATCATGGACTCGCTGCGCTACTGGGTCAGCGACATGCATGTCGACGGCTTCCGCTTCGAC

CTCGCGGCCACCCTGGCCCGGCAGTTCCACGAGGTGGACCGGCTGTCGTCGTTCTTCGAC

CTGGTCCAGCAGGACCCGGTGGTCTCCCAGGTGAAGCTGATCGCCGAGCCGTGGGACGTC

GGCGAGGGCGGCTACCAGGTGGGCAACTTCCCGCCGCTGTGGACCGAGTGGAACGGCAAG

TACCGCGACACGGTGCGGGACATGTGGCGGGGCGAGCCGCGTACGCTCGCGGAGTTCGCC
```

-continued

```
TCCCGCCTGACGGGCTCGTCGGACCTCTACCAGGACGACGGCCGCCGTCCCCTCGCCTCC

ATCAACTTCGTCACCTGCCACGACGGTTTCACCCTGCACGACCTCGTCGCGTACAACGACA

AGCACAACCAGGCCAACGGCGAGGACAACCGGGACGGGGAGAGCCACAACCGGTCCTGGA

ACTGCGGGGCCGAGGGCGACACCGACGATCCGGCGGTGCTGGCGTTGCGGGCGCGCCAGA

TGCGCAACTTCATCGCCACGCTGATGCTCTCGCAGGGCGTGCCGATGCTCAGCCACGGGA

TGAGTTCGCGCGCACCCAGGGCGGCAACAACAACGCGTACTGCCAGGACGGCGAGCTGTC

GTGGGTGGCGTGGCCCGAGGACGGCAGCGAGCTGCTGGAGTTCACGCGCGCGATGGTGTG

GCTGCGGCGCGACCATCCGGTCTTCCGGCGCCGCCGCTTCTTCCACGGGCGGCCGGTGGA

GGGCACGCACGACGAGCTGTCGGACATCGTCTGGTTCACGCCGACGGGTGAGGAGATGAT

CCAGCGCGACTGGGATTCGGCGCAGGCACGGGCGCTGACGGTGTTCCTCAACGGCACCGC

GATCTCCGAGCCCGGCCCACGCGGAGAGCGGATCTCGGACGACTCCTTCCTGTTGATGTTC

AACGCCTCCCCGAAGTCGCTGGAGTTCGTGGTGCCGGTCGACCACGGCCGCCAGTGGCAG

GTCGTCGTCGACACGGCACGCACGGACGGGATCCCGCCGGGCACGGTCGCGAAGGTCAAG

GCCGGGACCGGCTGACGCTGGTGGACCGGAGCCTCACGGTGTTGCAGCGGCCGGCCTGA
```

In one embodiment, the bacterium of the present disclosure is a bacterium in which a function of transaldolase is deleted or attenuated. In another embodiment, the bacterium of the present disclosure is a bacterium in which a function of propionyl CoA carboxylase is deleted or attenuated. In yet another embodiment, the bacterium of the present disclosure is a bacterium in which a function of trehalose synthase is deleted or attenuated. In another embodiment, the bacterium of the present disclosure is a bacterium in which at least one or more of the above functions are deleted or attenuated, such as a bacterium in which the functions of transaldolase and propionyl CoA carboxylase are deleted or attenuated, a bacterium in which the functions transaldolase and trehalose synthase are deleted or attenuated, or a bacterium in which the functions transaldolase, propionyl CoA carboxylase and trehalose synthase are deleted or attenuated.

In one embodiment, a function of an enzyme may be controlled by a DNA sequence encoding the protein, may be controlled at a transcriptional stage of the protein, may be controlled at a translational stage of the protein, or may be controlled at a post-translational stage of the protein. Preferably, a function of an enzyme is controlled by the DNA sequence encoding the protein.

In one embodiment, a function of an enzyme may be controlled by a DNA sequence encoding the protein, for example, the function may be deleted or attenuated by a mutation in the DNA sequence encoding the protein.

In one embodiment, a function of an enzyme may be controlled at a transcriptional stage of the protein, for example, the function may be deleted or attenuated by modifying a function of a cis or trans element of the DNA sequence encoding the protein.

In one embodiment, a function of an enzyme may be controlled at a translational stage of the protein, for example, the function may be deleted or attenuated by a mutation of the Shine-Dalgarno sequence for translation of the protein.

In one embodiment, a function of an enzyme may be controlled at a post-translational stage of the protein, for example, the function may be deleted or attenuated by treating the protein with an inhibitor.

In the present disclosure, a mutation includes a substitution, an addition, a deletion or a recombination.

Those skilled in the art may, for example, confirm a mutation of a gene encoding a protein, confirm a transcription of the protein, or confirm an activity the protein or an amount of the protein according to known techniques, to confirm whether the enzyme function is deleted or attenuated.

A function of an enzyme may be deleted or attenuated under a condition where a bacterium is used for a production of sedoheptulose. A deletion of an enzyme function refers to a state in which the function of the enzyme of a bacterium used in the present invention cannot be confirmed by those skilled in the art based on known techniques. Attenuation of an enzyme function refers to a state in which the function of the enzyme of a bacterium used in the present invention is attenuated as compared with normal state. More specifically, for example, attenuation of an enzyme function is a state in which the function is 90%, 80%, 70%, 60%, 50%, 40%, 30%, 20%, 10%, 5%, 2.5% or less than 1% as compared to the function when culturing a wild type bacteria under a normal culture condition. For example, in the case of attenuation due to an introduction of a mutation, comparison may be made under the same culture condition as in the wild type, and in the case of attenuation due to an inhibitor, comparison may be made under the same conditions except for presence or absence of the inhibitor.

Examples of a bacterium in the present disclosure include, but not limited to, actinomycete, *Escherichia coli* and *Bacillus subtilis*, a bacterium belonging to *Flavobacterium*, and a bacterium belonging to *Achromobacter*. In a preferred embodiment, the bacterium is actinomycete, *Bacillus subtilis*, a bacterium belonging to *Flavobacterium*, or a bacterium belonging to *Achromobacter*. In a more preferred embodiment, the bacterium is actinomycete.

In the present disclosure, "actinomycete" refers to a Gram-positive bacterium belonging to the phylum actinomycete (Actinobacteria). "Actinomycete" includes, but not limited to, for example, *Streptomyces* genus such as *Streptomyces lividans, Streptomyces violaceoruber, Streptomyces coelicolor, Streptomyces avermitilis*, and *Streptomyces griseus*; *Actinosynnema* genus such as *Actinosynnema pretiosum*, and *Actinosynnema mirum*; *Pseudonocardia* genus such as *Pseudonocardia autotrophica, Pseudonocardia ther-*

*mophila*; and *Corynebacterium* genus such as *Corynebacterium glutamicum*. In a preferred embodiment, the actinomycete is a bacterium belonging to *Streptomyces* or *Corynebacterium* genus, more preferably a bacterium belonging to *Streptomyces* genus, and even more preferably, the bacterium belonging to *Streptomyces* genus is *Streptomyces lividans* or *Streptomyces avermitilis*. The route for obtaining actinomycete is not particularly limited, and for example, it may be isolated from the soil, or may be obtained from a microorganism depository institution.

In the present disclosure, a bacterium used in a production of sedoheptulose is a bacterium that may biosynthesize sedoheptulose. For example, the bacterium used in a production of sedoheptulose is a bacterium having a sedoheptulose biosynthetic enzyme gene. The bacterium used for the production of sedoheptulose may be a wild type strain or a strain that have been artificially mutated. Examples of an artificial mutagenesis include a gene recombination, UV irradiation, X-ray irradiation, and a treatment with a mutagen. The bacterium used for the production of sedoheptulose may be a naturally occurring mutant strain. The bacterium used for the production of sedoheptulose also includes a bacterium having a homologous or heterologous sedoheptulose biosynthetic enzyme gene. For example, the bacterium used for the production of sedoheptulose may be a bacterium in which a heterologous sedoheptulose biosynthetic enzyme gene has been introduced by gene recombination. A method widely known in the art may be used to introduce the heterologous gene into the above-mentioned bacterium.

In the present disclosure, sedoheptulose may be produced intracellularly or extracellularly, preferably extracellularly. In the present disclosure, "bacterial cells" refers to bacterial cells. In addition, in the present disclosure, the "extracellular culture solution" refers to a portion of the culture solution obtained by culturing the bacterium and excluding the bacterial cells from the solution. That is, the extracellular culture solution comprises, for example, various components contained in the medium used for culture, and substances produced by a bacterium during culture.

In the present disclosure, a method for separating the bacterial cells and the extracellular culture solution is appropriately selected by those skilled in the art. For example, the culture solution obtained by culturing the bacterium may be subjected to centrifugation to separate the bacterial cells and the extracellular culture solution. As the centrifugation conditions such as temperature, time and speed, a well-known condition to a skilled person in the art may be used depending on the type of the bacterium used for culture. Alternatively, the bacterial cells and the extracellular culture solution may be separated by filtering the culture solution obtained by culturing the bacterium using an appropriate filtration membrane.

In the present disclosure, the separated extracellular culture solution itself may be used, or may be dried to be used as a composition containing sedoheptulose, or the produced sedoheptulose may be recovered from the extracellular culture solution. The term "recovery" means to obtain a solution mainly containing sedoheptulose, excluding various components and/or a bacterial cell contained in the medium used for culture. The proportion of sedoheptulose in the solution mainly containing sedoheptulose may be appropriately determined by those skilled in the art according to the purpose. A produced sedoheptulose may also be recovered as sedoheptulosan by acid treatment (Patent literature 5).

The produced sedoheptulose may be appropriately converted in or out of the cells to achieve a purpose by a technique known to those skilled in the art. Sedoheptulose may be converted chemically, enzymatically, or physicochemically, including phosphorylation, isomerization, cyclization, polymerization, acylation, galloylation, and dehydration cyclization. Converted sedoheptulose is for example sedoheptulose-7-phosphate, 7-O-galloyl-D-sedoheptulose and sedoheptulosan.

In one embodiment, a specific example of the production amount of sedoheptulose is, for example, preferably 3 g/L or more, more preferably 5 g/L or more in 7 days, or preferably 5 g/L or more, more preferably 10 g/L or more in 9 days. In still another specific example, the maximum sedoheptulose production amount during culture is preferably 5 g/L or more, more preferably 10 g/L or more, still more preferably 25 g/L or more.

According to the present disclosure, productivity of sedoheptulose by a bacterium may be improved. An improvement of productivity of sedoheptulose due to a deletion or attenuation of specific enzyme function means increase of productivity of sedoheptulose by the deletion or attenuation of specific enzyme function, or decrease of time until reaching specific productivity of sedoheptulose by the deletion or attenuation of specific enzyme function. More specifically, for example, 2 times or more, preferably 3 times or more, and more preferably 4 times or more of sedoheptulose is produced as compared with the case of culturing a wild type bacterium under normal culture conditions for 10 days of culture. In addition, when a wild type bacterium does not produce sedoheptulose under normal culture conditions, it may be allowed to produce sedoheptulose by a deletion or attenuation of the function of a specific enzyme.

In the production of sedoheptulose using a bacterium, those skilled in the art may appropriately change the culture conditions of the bacterium. A Culture condition of the bacterium may be changed by, for example, temperature, a carbon source, a nitrogen source, culture time, medium, oxygen content, pH, or an additive such as an antibiotic, for example, tetracycline (Non-patent literature 5).

In another embodiment, the present invention provides the above-described method of the present invention, further comprising the step of adding a carbon source to the medium. The further addition may be carried out at any time during culture of the bacterium, and it may be carried out continuously or intermittently. Desirably, the carbon source is further added so that the bacterium will not lyse. The lysis of a bacterium may be confirmed, for example, by measuring the pH of the culture solution. For actinomycete, desirably, the carbon source is further added so that the pH of the medium does not exceed 8.0. The lysis of a bacterium may also be confirmed by a decrease in the amount of the bacterium in the medium.

A Carbon source used in the present invention include, but not limited to, glucose, sucrose, fructose, mannitol, sorbitol, galactose, maltose, xylose, glycerol, ribose, gluconolactone or gluconic acid or salts thereof. In a preferred embodiment, the carbon source is glucose or glycerol. In another preferred embodiment, the carbon source does not contain ribose.

When the carbon source in the medium is consumed, various organic acids are produced as metabolites and the medium is acidified. The production of sedoheptulose by a bacterium is reduced due to acidification of the medium. Therefore, an alkalizing agent may be added to the medium so that the medium is not acidified. In case that actinomycete is used, an alkalizing agent is added to the medium so that the pH of the medium is not lowered below 5.0, preferably 5.5. The alkalizing agent includes, but not limited to, a carbonate such as calcium carbonate, magnesium carbonate, sodium carbonate, and sodium hydrogen carbonate, a hydroxide such as sodium hydroxide, potassium hydroxide, calcium hydroxide and magnesium hydroxide, ammonia, urea, and Calcium oxide. In a preferred embodiment, the alkalizing agent used in the present invention is a carbonate such as calcium carbonate, magnesium carbonate, sodium carbonate and sodium hydrogen carbonate. The alkalizing agent may be added to the medium before culture or may be added during culture. Further, the addition of the alkalizing agent may be continuous or intermittent addition. The amount of alkalizing agent to be added may be determined by measuring the pH of the medium, without difficulty. A pH may be measured by a known method, for example, using a pH meter.

Therefore, it may be effective for increasing the production of sedoheptulose to add a carbon source which is a raw material of sedoheptulose to the medium that may prevent a pH increase of the medium and to add an alkalizing agent to prevent a pH decrease of the medium.

In the present invention, the medium for culturing the bacterium and other culture conditions (for example temperature, time, pH, presence or absence of stirring) are appropriately selected by those skilled in the art according to the type of the bacterium to be cultured. Examples of more specific conditions include, but not limited to, pH 5 to 8, temperature 10 to 45° C., time 5 to 50 days.

The invention further provides the following aspects:
(1) a method for improving productivity of sedoheptulose, comprising culturing a bacterium in which a function of transaldolase is deleted or attenuated;
(2) the method according to (1), where the bacterium is a bacterium in which a function of propionyl CoA carboxylase and/or a function of trehalose synthase is/are further deleted or attenuated;
(3) the method according to (1) or (2), where the bacterium is actinomycete, *Bacillus subtilis*, a bacterium belonging to *Flavobacterium*, or a bacterium belonging to *Achromobacter*;
(4) the method according to (3), where the bacterium is actinomycete;
(5) the method according to (4), where the actinomycete is a bacterium belonging to *Streptomyces*; or
(6) the method according to (5), where the bacterium belonging to *Streptomyces* is *Streptomyces lividans* or *Streptomyces avermitilis*.

Hereinafter, the present invention will be described specifically and in detail with reference to Examples, but the Examples are used for illustrating the present invention and are not intended to limit the present invention.

EXAMPLE

Example 1

1. Production of Sedoheptulose Using *Streptomyces*

The inventor of the present application used *Streptomyces lividans* and *Streptomyces avermitilis* as a host to prepare a sedoheptulose producing strain, and examined the amount of sedoheptulose in the culture solution.

1-1. A Disruption of a Transaldolase Gene 1-1-1. A Disruption of a Transaldolase Gene in *Streptomyces lividans*

The transaldolase gene (SLI_2249) of *Streptomyces lividans* strain 1326 (NITE deposit number: NBRC 15675) was disrupted by homologous recombination. Transformation of *Streptomyces lividans* was performed according to a conventionally known method. Positions 1 to 1119 of SLI_2249 were disrupted and the gene disruption was confirmed using the primers AAGATCCCGGTCTTCGAGGCGGGCA-AGGGC (SEQ ID NO: 25) and GCGGCGTAGGTGTC-GGTCTTCGACTTGGGG (SEQ ID NO: 26).

1-1-2. A Disruption of a Trehalose Synthase Gene in *Streptomyces lividans*

The transaldolase gene (SLI_2249)-disrupted strain for *Streptomyces lividans* 1326 was used as a host, and the trehalose synthase gene (SLI_7555) was disrupted by homologous recombination. Transformation of *Streptomyces lividans* was performed according to a conventionally known method. Positions 1 to 1719 of SLI_7555 were disrupted and the gene disruption was confirmed using the primers CAAAGGCCGCAACAACACCCTCTCCGCC (SEQ ID NO: 27) and TAGCCCGCGCAGAACG-CCTCCCGGCA (SEQ ID NO: 28).

1-1-3. A Disruption of a Propionyl CoA Carboxylase Gene in *Streptomyces lividans*

The transaldolase gene (SLI_2249)-disrupted strain for *Streptomyces lividans* 1326 was used as a host, and the propionyl CoA carboxylase gene (SLI_5198) was disrupted by homologous recombination. Transformation of *Streptomyces lividans* was performed according to a conventionally known method. Positions 1 to 1593 of SLI_5198 were disrupted, and the gene disruption was confirmed using the primers CCCAGGATGAGCCCCTCGAGGCGCAG (SEQ ID NO: 29) and CTGATCGTGCTGCTGCTGATGAC-GTACGA (SEQ ID NO: 30).

1-1-4. A Disruption of a Transaldolase Gene in *Streptomyces avermitilis*

The transaldolase gene (sav6314) of *Streptomyces avermitilis* strain MA-4680 (NITE deposit number: NBRC 14893) was disrupted by homologous recombination. Homologous recombination of *Streptomyces avermitilis* was performed according to a conventionally known method. The positions 1 to 1119 of sav6314 were disrupted, and the gene disruption was confirmed using the primers TCCGCCGACCTGGCCGGCTCGAACAACACC (SEQ ID NO: 31) and GCCAGCCGGCCGCGTACT-GTCCGCGGACGG (SEQ ID NO: 32).

1-2. Preculture of *Streptomyces lividans* and *Streptomyces avermitilis*

A glycerol stock of spores of *Streptomyces: Streptomyces lividans* strain 1326, *Streptomyces lividans* strain 1326ΔSLI_2249, *Streptomyces lividans* strain 1326ΔSLI_2249ΔSLI_5198, *Streptomyces lividans* 1326ΔSLI_2249ΔSLI_7555 strain, *Streptomyces avermitilis* MA-4680 strain and *Streptomyces avermitilis* MA-4680Δsav6314 that were produced in 1-1 above was added to 5 mL of TSB medium (see Table 1 below). These actinomycetes were cultured at 28° C., 160 rpm for 72 hours with shaking.

1-3. Main Culture of *Streptomyces lividans* and *Streptomyces avermitilis*

A 0.1% volume of preculture solution was added to 50 mL of TSB medium (see Table 1 below) in a 500 mL baffled flask. Glucose was further added to the TSB medium at the start of culture so that the initial glucose concentration was 80 g/L. During culture, the culture was shaken at 28° C., 160 rpm for 2 weeks while glucose was supplemented so that glucose was not exhausted.

TABLE 1

| TSB medium | |
| --- | --- |
| Pancreatic digest of casein | 17 g (1.7%) |
| Papaic digest of soybean | 3 g (0.3%) |
| Glucose | 2.5 g (0.25%) |
| NaCl | 5 g (0.5%) |
| $K_2HPO_4$ | 2.5 g (0.25%) |

1-4. Sedoheptulose Measurement

During the main culture, 1 mL of the culture solution was collected at a predetermined time and optical density at 600 nm was measured. The collected culture solution was centrifuged at 14000 rpm for 20 minutes to obtain a culture solution sample. The production amount of sedoheptulose in the culture solution sample was measured by HPLC. The HPLC measurement conditions are as shown in the table below.

TABLE 2

| | |
| --- | --- |
| Column: | Aminex HPX-87C (9 μm; 7.8 φmm × 300 mm) (Bio-Rad Laboratories, Inc.) |
| Solvent: | $H_2O$ |
| Detector: | RID |
| Standard sample: | Sedoheptulose (Sigma-Aldrich Co. LLC) |
| Flow rate: | 0.6 mL/min |
| Column temperature: | 85° C. |
| Retention time: | Sedoheptulose: around 12 min |

1-5. Result

Figure 2:
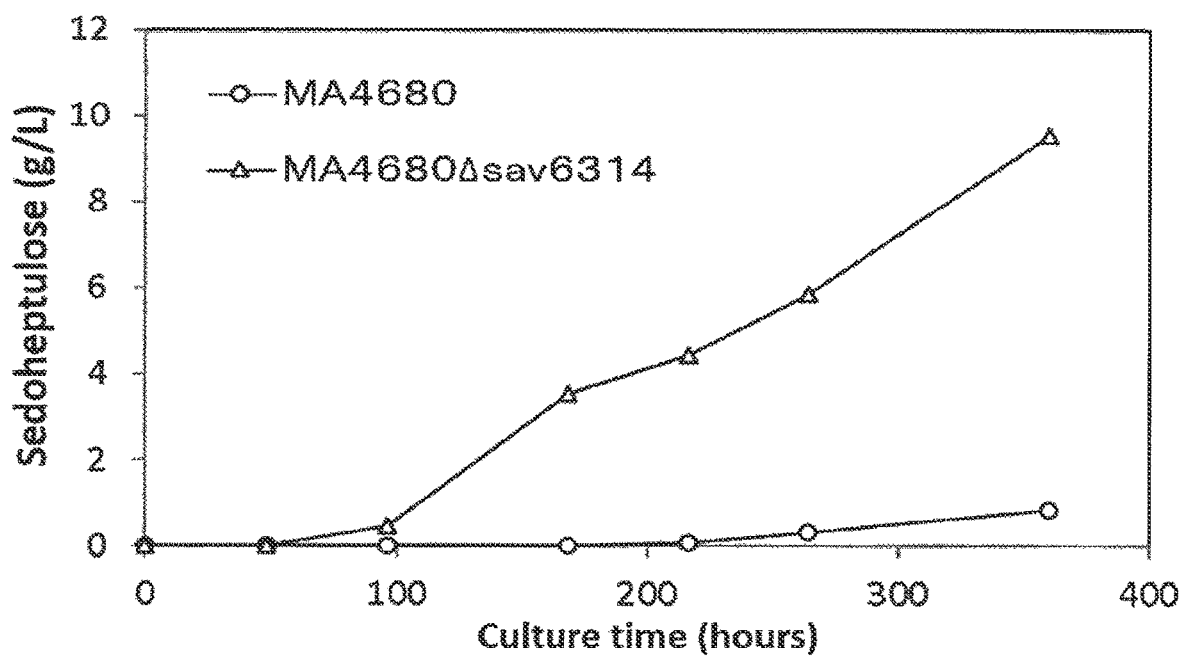
FIG. 2 shows the results of the production of sedoheptulose using *Streptomyces avermitilis* MA-4680 strain.
Figure 3:
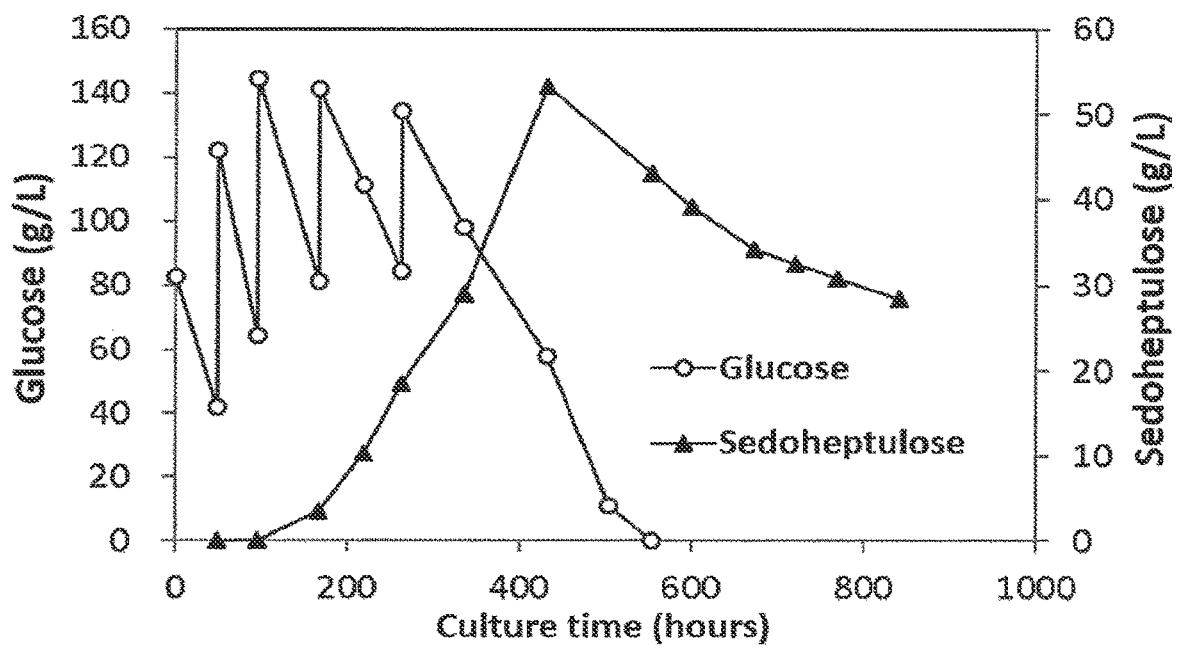
FIG. 3 shows changes in the productivity of sedoheptulose after culturing the *Streptomyces lividans* 1326ΔSLI_2249ΔSLI_5198 strain for a long period of time and stopping the supplemental addition of glucose.

The results for the *Streptomyces lividans* strain 1326 are shown in FIG. 1, and the results for the *Streptomyces avermitilis* strain MA-4680 are shown in FIG. 2. For the *Streptomyces lividans* strain 1326, a production of sedoheptulose could not be confirmed after 2 weeks of culture. The *Streptomyces lividans* strain 1326ΔSLI_2249 produced up to 5.7 g/L of sedoheptulose in about 9 days of culture. The *Streptomyces lividans* strain 1326ΔSLI_2249 ΔSLI_5198 produced 28.8 g/L of sedoheptulose in about 2 weeks of culture. The *Streptomyces lividans* strain 1326ΔSLI_2249 ΔSLI_7555 produced 13.0 g/L of sedoheptulose in about 11 days of culture. The *Streptomyces avermitilis* strain MA-4680 produced 0.9 g/L of sedoheptulose after 2 weeks of culture. The *Streptomyces avermitilis* strain MA-4680Δsav6314 produced 9.5 g/L sedoheptulose in 2 weeks of culture. In *Streptomyces lividans* and *Streptomyces avermitilis*, a disruption of the transaldolase gene significantly increased productivity of sedoheptulose. Furthermore, a combination of a disruption of the trehalose synthase gene or the propionyl CoA carboxylase gene with a disruption of the transaldolase gene disruption, productivity of sedoheptulose was significantly improved. FIG. 3 shows changes in productivity of sedoheptulose after the *Streptomyces lividans* strain 1326ΔSLI_2249ΔSLI_5198 was cultured for a long period of time and the supplemental addition of glucose was stopped. Although the production of sedoheptulose was increased over time and sedoheptulose was produced at a maximum of 53.3 g/L in 431 hours during the supplemental addition of glucose, when the supplementation of glucose was stopped and glucose became depleted, it is observed that the productivity of sedoheptulose was decreased.

INDUSTRIAL AVAILABILITY

According to the present invention, there is to provide a method for producing sedoheptulose with a bacterium, a method for improving productivity of sedoheptulose with the bacterium, and the bacterium.

The invention claimed is:

1. A method for an improved production of sedoheptulose as compared to wildtype, the method comprising: culturing a bacterium in which a function of transaldolase is deleted or attenuated; and collecting an extracellular culture solution comprising sedoheptulose.

2. The method of claim 1, wherein the bacterium is a bacterium in which a function of propionyl CoA carboxylase is further deleted or attenuated.

3. The method of claim 1, wherein the bacterium is actinomycete, *Bacillus subtilis*, a bacterium belonging to *Flavobacterium*, or a bacterium belonging to *Achromobacter*.

4. The method of claim 3, wherein the bacterium is actinomycete.

5. The method of claim 4, wherein the actinomycete is a bacterium belonging to *Streptomyces*.

6. The method of claim 5, wherein the bacterium belonging to *Streptomyces* is *Streptomyces lividans* or *Streptomyces avermitilis*.

7. The method of claim 1, wherein the bacterium is a bacterium in which a function of trehalose synthase is further deleted or attenuated.

8. The method of claim 1, wherein the bacterium is *Bacillus subtilis*.

9. The method of claim 1, wherein the bacterium is a bacterium belonging to *Flavobacterium*.

10. The method of claim 1, wherein the bacterium is a bacterium belonging to *Achromobacter*.

* * * * *